United States Patent [19]
Hori

[11] Patent Number: 5,895,350
[45] Date of Patent: Apr. 20, 1999

[54] ELECTRONIC ENDOSCOPE

[75] Inventor: Koichiro Hori, Framingham, Mass.

[73] Assignee: Vista Medical Technologies, Inc., Carlsbad, Calif.

[21] Appl. No.: 08/895,386

[22] Filed: Jul. 16, 1997

Related U.S. Application Data

[63] Continuation of application No. 08/581,307, Dec. 28, 1995, abandoned, which is a continuation of application No. 08/067,140, May 25, 1993, abandoned, which is a continuation-in-part of application No. 07/967,996, Oct. 28, 1992, abandoned.

[51] Int. Cl.$^6$ .................................................. A61B 1/05
[52] U.S. Cl. ................................................. 600/167; 600/109
[58] Field of Search ................................ 600/103, 109, 600/112, 113, 131, 160, 167, 168, 182; 385/117, 119; 348/65, 71, 76; 359/698, 367

[56] References Cited

U.S. PATENT DOCUMENTS

| | | | |
|---|---|---|---|
| 3,091,235 | 5/1963 | Richards. | |
| 3,261,349 | 7/1966 | Wallace. | |
| 3,294,085 | 12/1966 | Wallace | 385/117 X |
| 3,496,931 | 2/1970 | Pilling. | |
| 3,581,376 | 6/1971 | Pilling. | |
| 3,592,199 | 7/1971 | Ostensen. | |
| 3,804,081 | 4/1974 | Kinoshita et al. | 128/6 |
| 3,817,251 | 6/1974 | Hasson. | |
| 3,819,267 | 6/1974 | Kawahara | 128/6 X |
| 4,074,306 | 2/1978 | Kakinuma et al. | |
| 4,085,756 | 4/1978 | Weaver. | |
| 4,261,344 | 4/1981 | Moore et al. | |
| 4,313,431 | 2/1982 | Frank. | |
| 4,327,738 | 5/1982 | Green et al. | |
| 4,354,730 | 10/1982 | Bel. | |
| 4,392,485 | 7/1983 | Hiltebrandt. | |
| 4,444,462 | 4/1984 | Ono et al. | |
| 4,445,892 | 5/1984 | Hussein et al. | |
| 4,488,039 | 12/1984 | Sato et al. | 359/698 |
| 4,527,552 | 7/1985 | Hattori. | |
| 4,539,976 | 9/1985 | Sharpe. | |
| 4,558,691 | 12/1985 | Okada | 128/6 |
| 4,561,430 | 12/1985 | Walsh. | |
| 4,562,831 | 1/1986 | Murakoshi et al. | |
| 4,597,380 | 7/1986 | Raif et al. | |
| 4,600,939 | 7/1986 | Sluyter et al. | |
| 4,600,940 | 7/1986 | Sluyter et al. | |
| 4,601,284 | 7/1986 | Arakawa et al. | |
| 4,617,933 | 10/1986 | Hasson. | |
| 4,620,769 | 11/1986 | Tsuno | 128/6 X |
| 4,651,201 | 3/1987 | Schoolman. | |
| 4,667,229 | 5/1987 | Cooper et al. | |
| 4,710,807 | 12/1987 | Chikama. | |
| 4,760,840 | 8/1988 | Fournier, Jr. et al. | |
| 4,777,524 | 10/1988 | Nakajima et al. | 128/4 X |
| 4,784,144 | 11/1988 | Ono et al. | |
| 4,807,026 | 2/1989 | Nishioka et al. | 128/6 X |

(List continued on next page.)

FOREIGN PATENT DOCUMENTS 6069620  4/1985  Japan.

*Primary Examiner*—John P. Leubecker
*Attorney, Agent, or Firm*—Pandiscio & Pandiscio

[57] ABSTRACT

An endoscope includes a hollow tube having a proximal end and a distal end, a window disposed in an aperture of the distal end of the tube, a lens disposed proximate the window in the distal end of the tube and a photodetector disposed proximate the objective lens in the distal end of the tube.

4 Claims, 16 Drawing Sheets

U.S. PATENT DOCUMENTS

| | | |
|---|---|---|
| 4,832,003 | 5/1989 | Yabe . |
| 4,846,154 | 7/1989 | MacAnally et al. . |
| 4,846,155 | 7/1989 | Kimura . |
| 4,850,342 | 7/1989 | Hashiguchi et al. . |
| 4,854,302 | 8/1989 | Alfred, III . |
| 4,862,873 | 9/1989 | Yajima et al. . |
| 4,865,018 | 9/1989 | Kanno et al. . |
| 4,867,136 | 9/1989 | Suzuki et al. . |
| 4,867,137 | 9/1989 | Takahashi . |
| 4,867,138 | 9/1989 | Kubota et al. . |
| 4,870,950 | 10/1989 | Kambara et al. . |
| 4,877,016 | 10/1989 | Kantor et al. . |
| 4,878,485 | 11/1989 | Adair . |
| 4,879,992 | 11/1989 | Nishigaki et al. . |
| 4,905,082 | 2/1990 | Nishigaki et al. . |
| 4,905,668 | 3/1990 | Ohsawa . |
| 4,924,853 | 5/1990 | Jones, Jr. et al. . |
| 4,979,497 | 12/1990 | Matsuura et al. . |
| 4,998,527 | 3/1991 | Meyer . |
| 5,010,876 | 4/1991 | Henley et al. . |
| 5,025,778 | 6/1991 | Silverstein et al. . |
| 5,027,792 | 7/1991 | Meyer . |
| 5,037,433 | 8/1991 | Wilk et al. . |
| 5,066,295 | 11/1991 | Kozak et al. . |
| 5,085,658 | 2/1992 | Meyer . |
| 5,166,787 | 11/1992 | Irion et al. . |
| 5,175,650 | 12/1992 | Takayama et al. . |
| 5,222,477 | 6/1993 | Lia .................................................. 128/6 |
| 5,305,121 | 4/1994 | Moll . |
| 5,575,757 | 11/1996 | Kennedy et al. ......................... 600/109 |

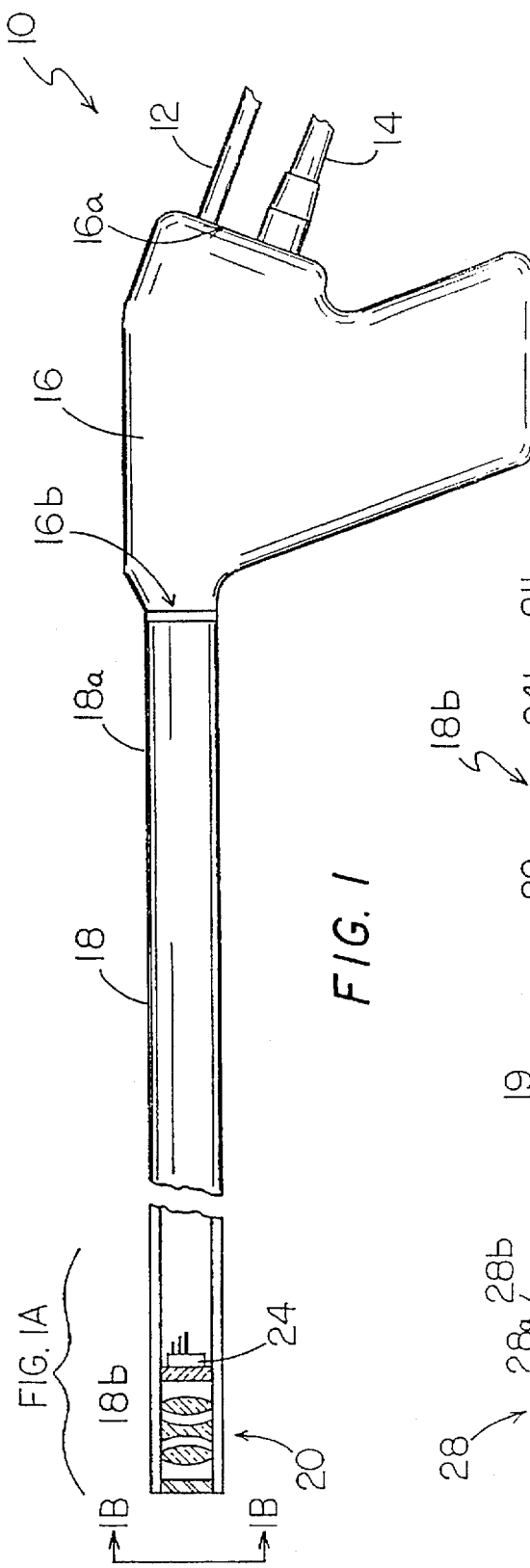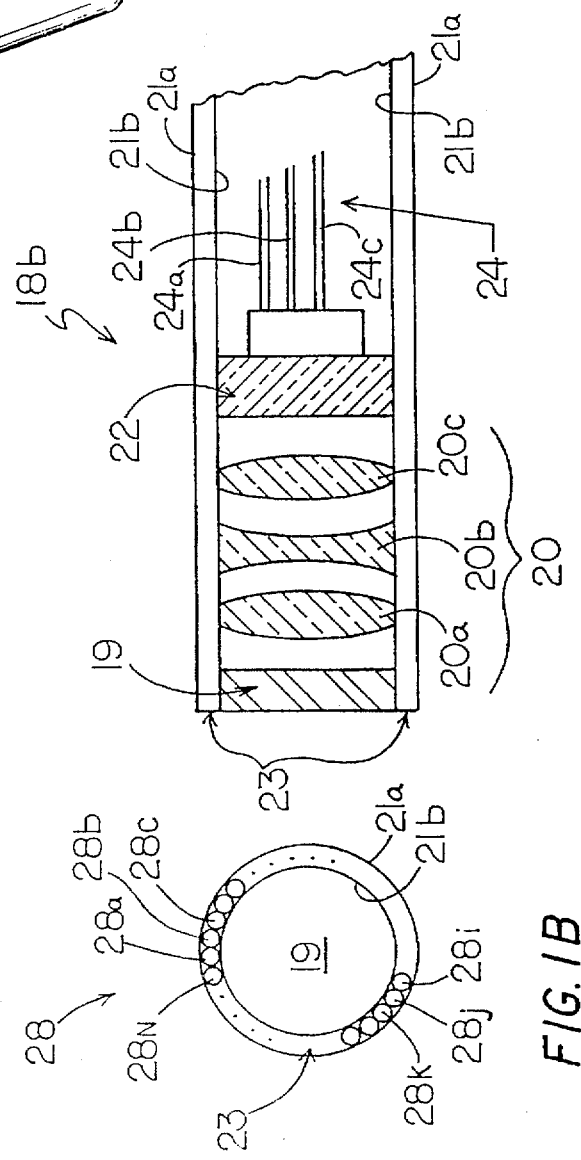
FIG. 1
FIG. 1A
FIG. 1B

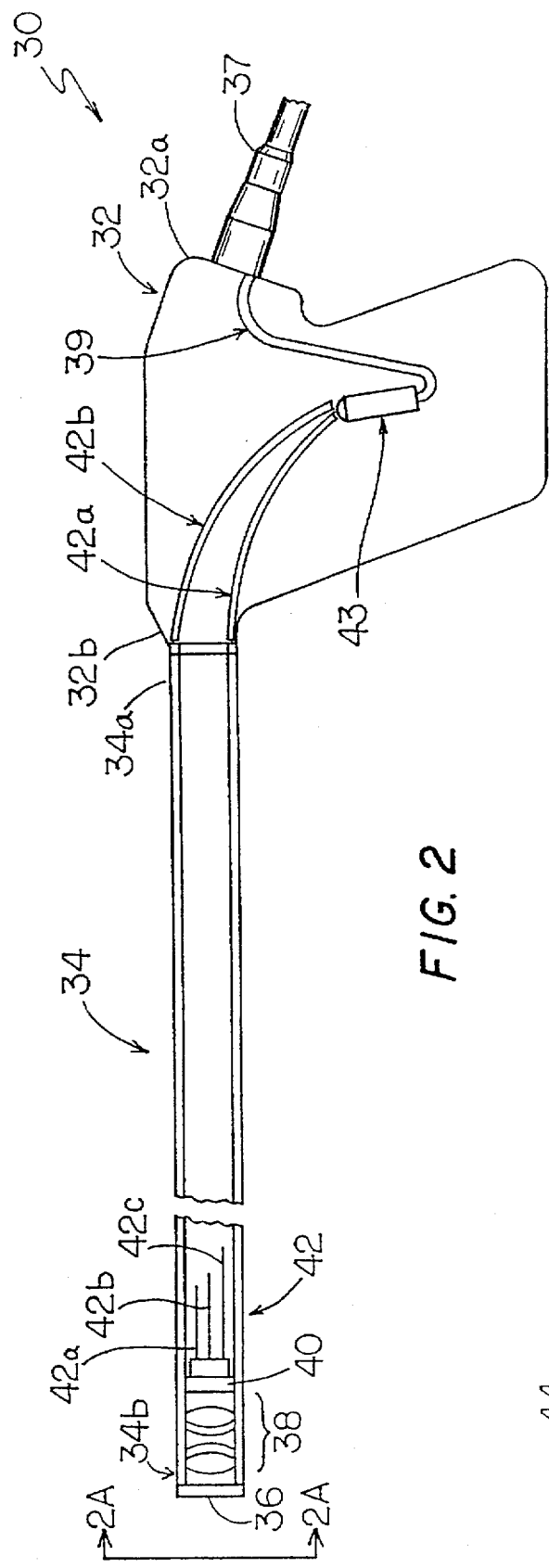
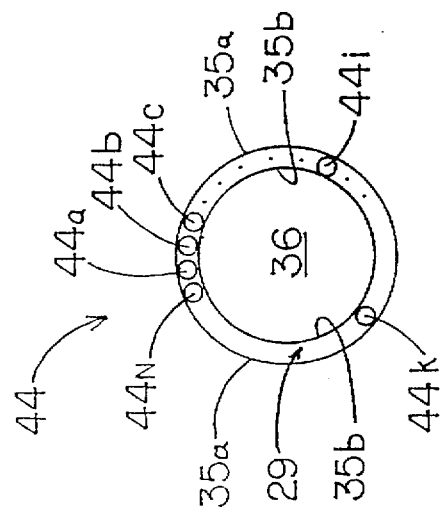
FIG. 2
FIG. 2A

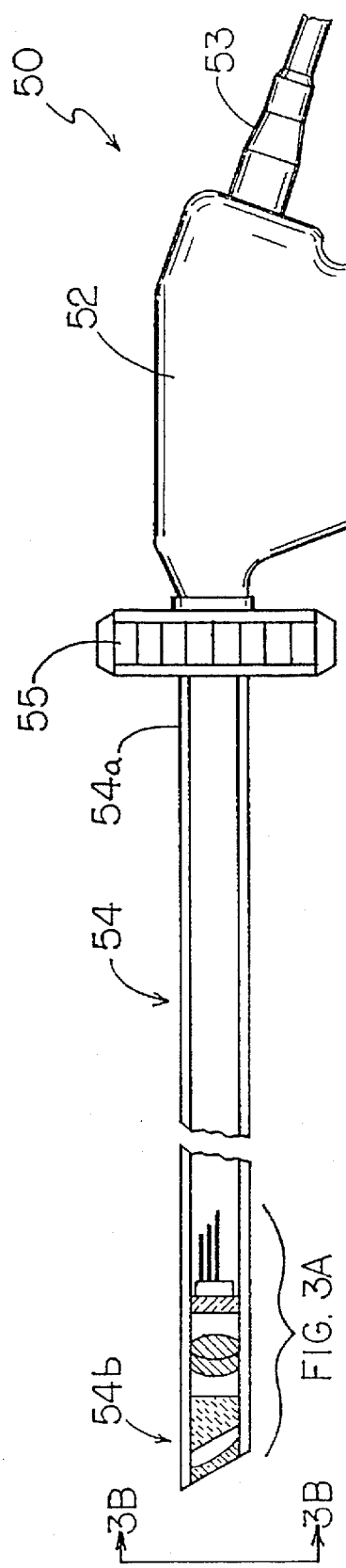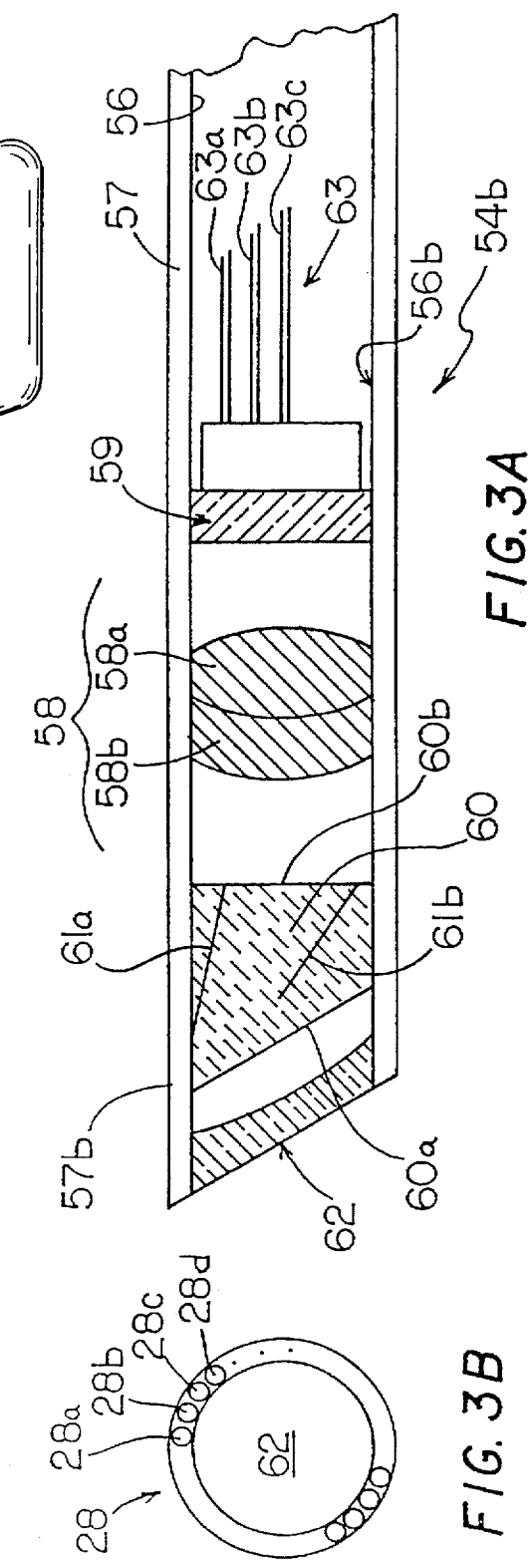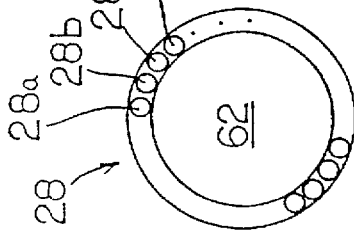

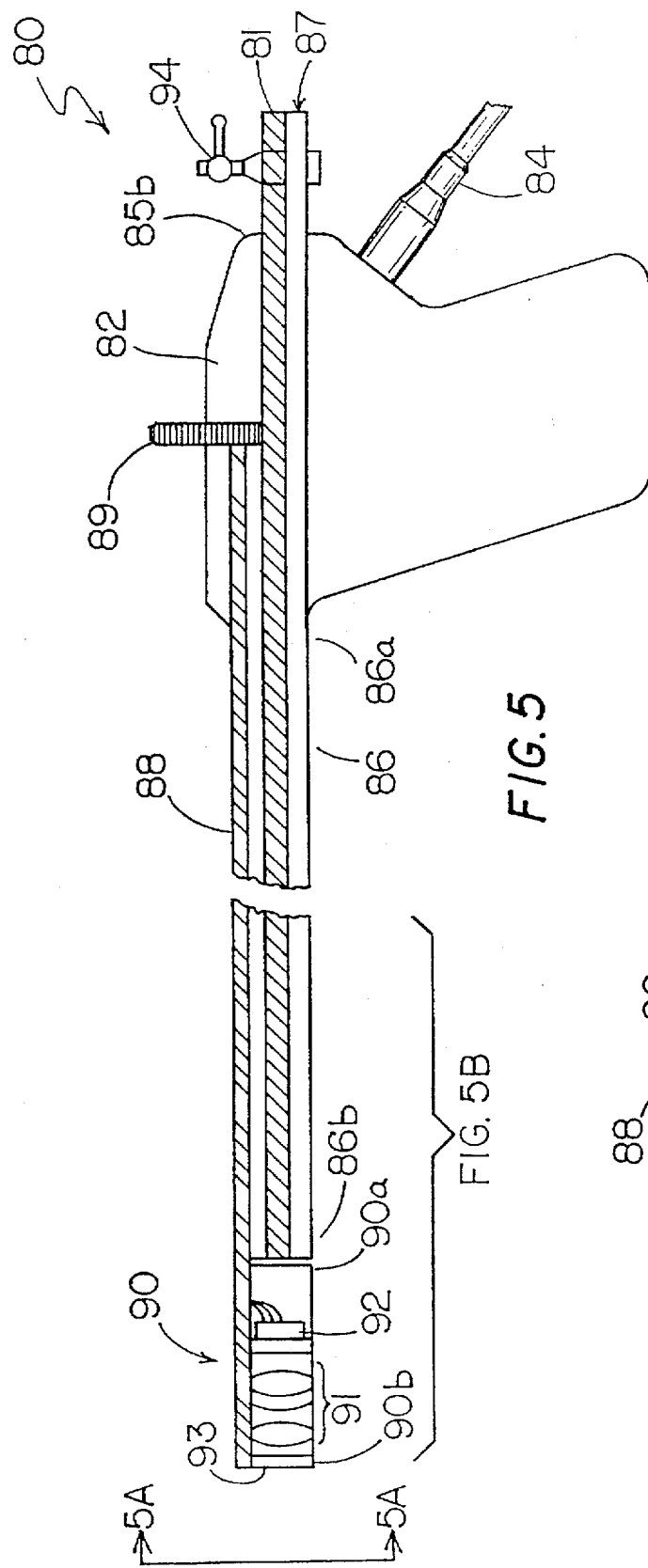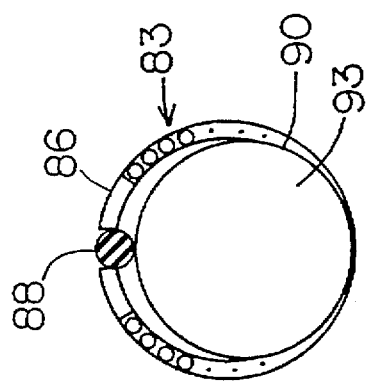
FIG. 5
FIG. 5A
FIG. 5B

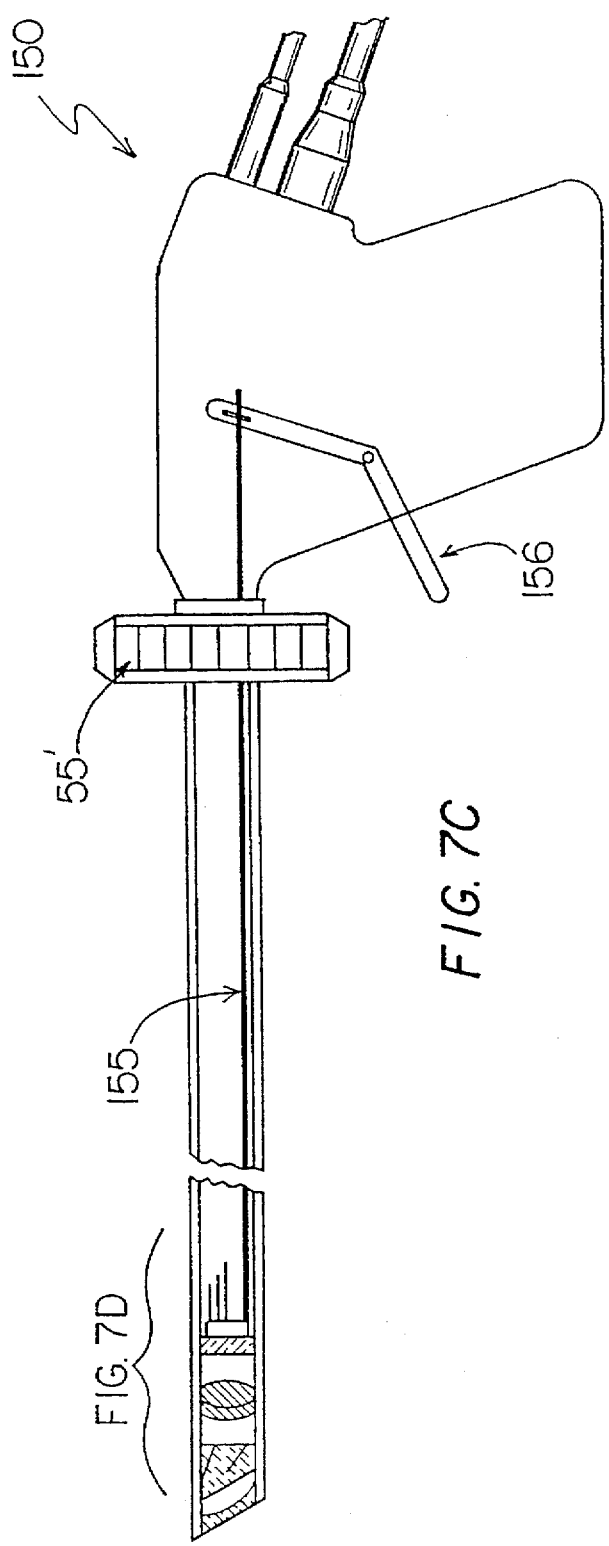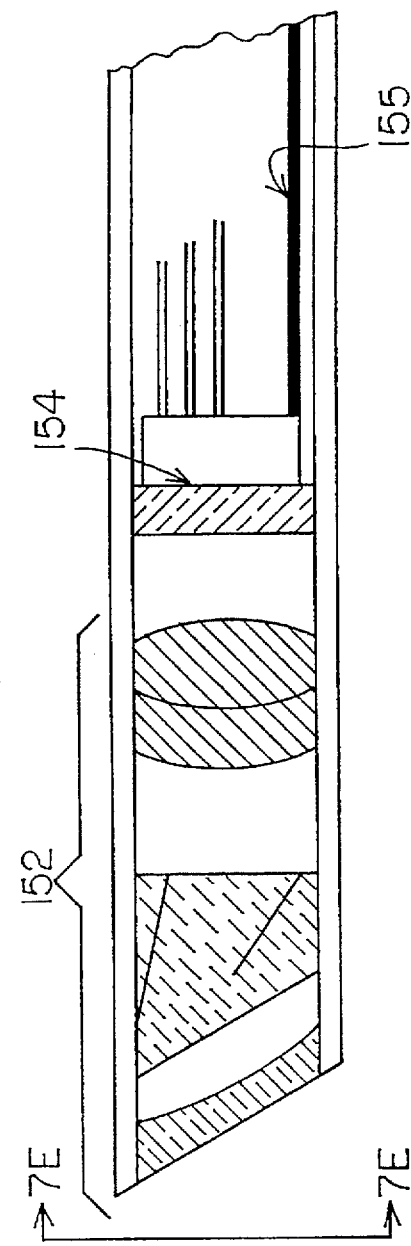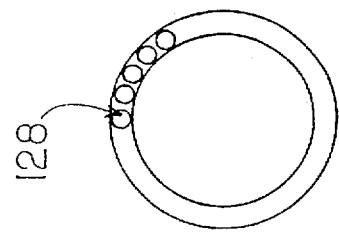
FIG. 7C
FIG. 7D
FIG. 7E

ELECTRONIC ENDOSCOPE

RELATED APPLICATION

This is a continuation of prior copending U.S. application Ser. No. 08/581,307, filed Dec. 28,1995, now abandoned, which is a continuation of prior copending U.S. application Ser. No. 08/067,140, filed May 25,1993, now abandoned, which is a continuation in part of prior copending U.S. application Ser. No. 07/967,996, filed Oct. 28, 1992, now abandoned.

BACKGROUND OF THE INVENTION

This invention relates generally to endoscopes and more particularly to electronic endoscopes.

As is known in the art, an endoscope generally includes an elongated hollow tube having a proximal or viewing end and a distal end. An optical path, including a plurality of lenses is disposed in the tube. An image provided to the distal end of the tube is transmitted along the optical path to the proximal end of the tube. The proximal end of the tube and thus the optical path typically terminate in an eye piece or in an objective plane of a microscope.

As is also known, such endoscopes may be used by physicians and others to view anatomical features of internal organs in a body cavity. In such applications, the physician inserts an endoscope into the body cavity of a patient to provide a clear view of an anatomical feature or body organ of the patient. This is especially true in the case of a surgeon who may have the need to see details of the anatomical features upon which a surgical procedure is to be performed.

As is also known, video cameras have taken a greater role in the surgical theater with the advent of lighter, smaller and higher resolution video cameras. Endoscopes may be fitted with such video cameras to allow the physician to view anatomical features of interest on a video monitor. Thus, there exists a trend to terminate the optical path of the endoscope in a video camera which may in turn be coupled to a video monitor.

One problem with such endoscopes however, is that each of the lenses in the optical path generally reflect from each surface thereof up to 1.5 percent (1.5%) of the light incident on each lens surface. When it is necessary or desirable to increase the length of the endoscope, it is necessary to increase the number of lenses in the optical path. An optical path having a large number of lenses provides a relatively large transmission loss to an image which is transmitted along the optical path from the distal end to the proximal end of the endoscope. This is especially true when the lenses are provided having a relatively small diameter. Thus, the image viewed on a video monitor coupled to the proximal end of the endoscope, for example, is relatively dim.

Furthermore, the lenses in the optical path generally reduce the contrast ratio and resolution of the image and also provide chromatic aberrations and geometrical distortions of the image. Moreover, it becomes increasingly more complex and difficult to align each of the lenses included in the optical path. This leads to an increase in the cost of manufacturing the endoscope.

SUMMARY OF THE INVENTION

In accordance with the present invention, an endoscope includes a hollow tube having a proximal end and a distal end, a window disposed in an aperture of the distal end of the tube, an objective lens disposed proximate the window in the distal end of the tube and a photodetector disposed proximate the objective lens in the distal end of the tube. With this particular arrangement an endoscope having a relatively short optical train is provided. The photodetector may be provided for example as a charge coupled device (CCD) image sensor disposed in the distal end of the tube. The CCD may be coupled to a video signal processing unit and subsequently to a video monitor. Thus, the endoscope may be provided having fewer lenses in the optical train between the distal and proximal end of the endoscope. Since each lens has a reflective surface, an optical train having fewer lenses has a concomitant decrease in optical transmission losses which occur therein compared with the optical transmission losses which occur in conventional endoscopes. Since less light is attenuated within the endoscope due to reflective and transmissive losses, less light is needed to illuminate a viewing area. Furthermore, an optical train having fewer lenses provides images having a reduced amount of chromatic aberration and geometrical distortions.

In accordance with a further aspect of the present invention, an endoscope includes a first tube having a proximal end and a distal end and a second tube disposed about and rotatable with respect to the first tube with a proximal end of the second tube terminated substantially coincident with the proximal end of the first tube and a distal end of the second tube terminated at an angle. The endoscope further includes an optical path disposed in and coupled to the distal end of the second tube and a photodetector disposed in and coupled to the distal end of the first tube. With this particular arrangement, an endoscope having a 360 degree field of view while transmitting images to a video monitor in a constant orientation is provided. The second tube having the optical path disposed therein may be rotated via a knob coupled thereto while the photodetector, which may be provided for example as a CCD image sensor, remains in a fixed position and is not rotated. Thus, the second tube may be rotated 360 degrees about a central longitudinal axis while the image transmitted to and viewed on the video monitor remains in a constant orientation. Furthermore, a field widening lens may be disposed in an aperture of the angled termination of the second tube.

In accordance with a still further aspect of the present invention a stereoscopic endoscopic viewing system includes a first hollow tube having a proximal end and a distal end, a first window disposed in an aperture of the distal end of the first tube and a optical train disposed proximate the window in the distal end of the first tube. A first photodetector is disposed proximate the optical path in the distal end of the first tube and a rod is coupled to the first hollow tube. The stereoscopic endoscopic viewing system further includes a second hollow tube having a proximal end and a distal end with the second hollow tube being coupled to and movable in response to the rod, a second window disposed in an aperture of the distal end of the second tube, a second optical train disposed proximate the window in the distal end of the second tube and a second photodetector disposed proximate the second optical train in the distal end of the second tube. With this particular arrangement, a stereoscopic endoscopic viewing system having increased separation between a pair of optical trains is provided. The first and second tubes of the endoscope may be aligned along a single longitudinal axis and inserted into a body cavity of a patient for example through a cannula as is generally known. Since the first and second tubes are concentrically aligned along a single longitudinal axis the endoscope may be inserted through a relatively small opening in a body wall of the patient. After the first and second tubes are inserted through the patient's body wall and into a body cavity through the cannula, the second tube may be rotated about the rod until the longitudinal axis of both the first and second tubes are separate and substantially parallel. The second tube may then be retracted via the rod a predetermined distance until the distal end of the second tube and the distal end of the first tube are substantially aligned in a single plane. The distance between the central longitudinal axis of the first tube and the central longitudinal axis of the second tube may be significantly wider than in conventional single tube systems having adjacently disposed optical trains. By providing a relatively wide separation between the optical paths, the stereoscopic endoscopic viewing system provides a better sense of depth perception or three-dimensional sensation when the images are converted to electrical signals via the photodetectors and coupled to a video monitor.

In accordance with a still further aspect of the present invention an endoscope includes a first tube having a proximal end and a distal end and a channel therethrough, a rod, and a second hollow tube having a proximal end juxtaposed the distal end of the first hollow tube and a distal end with the second hollow tube being coupled to and movable in response to the rod. The endoscope further includes a window disposed in an aperture of the distal end of the second tube, an optical train disposed proximate the window in the distal end of the second tube and a photodetector disposed proximate the optical train. With this particular arrangement an endoscope having an operative channel is provided. The central longitudinal axis of the first and second tubes may be aligned and the endoscope may be disposed through a cannula into a small incision made in a body wall of a patient to view a body cavity of the patient. The second tube may then be rotated about the rod such that a central longitudinal axis of the first tube and a central longitudinal axis of the second tube are substantially parallel and the channel in the first tube is exposed. The second tube may then be retracted via the rod such that the distal end of the first tube and the distal end of the second tube are substantially aligned in a single plane. Thus a surgeon for example may insert a surgical instrument through the operative channel of the endoscope and operate on a predetermined region of the patient. Furthermore, by rotating the second tube to expose the operative channel provided in the first tube, the operative channel may be provided having a relatively large diameter. Furthermore by placing the photodetector, which may be provided as a charge couple device image sensor for example, proximate the optical train in the distal end of the second tube, the operative endoscope of the present invention is significantly more light sensitive and provides less distortion to an image than do conventional designs. Thus, the operative endoscope has an operative channel having a larger diameter and provides a minimum amount of image degradation.

BRIEF DESCRIPTION OF THE DRAWINGS

The foregoing features of this invention as well as the invention itself may be more fully understood from the following detailed description of the drawings in which:

FIG. 1 is a side view of an electronic endoscope;

FIG. 1A is a cross sectional view of a portion of the electronic endoscope of FIG. 1;

FIG. 1B is a front view of the electronic endoscope of FIG. 1 taken along lines 1B—1B of FIG. 1;

FIG. 2 is cross-sectional view of an endoscope having an integral illumination assembly;

FIG. 2A is a front view of the endoscope of FIG. 2 taken along lines 2A—2A of FIG. 2;

FIG. 3 is a side view of an endoscope having a rotatable optical train;

FIG. 3A is a cross sectional view of a portion of the endoscope of FIG. 3;

FIG. 3B is a front view of the endoscope of FIG. 1;

FIGS. 7C–7E are a series of views of an endoscope having a rotatable optical train and a focusing mechanism;

DESCRIPTION OF THE PREFERRED EMBODIMENTS

Figure 4:
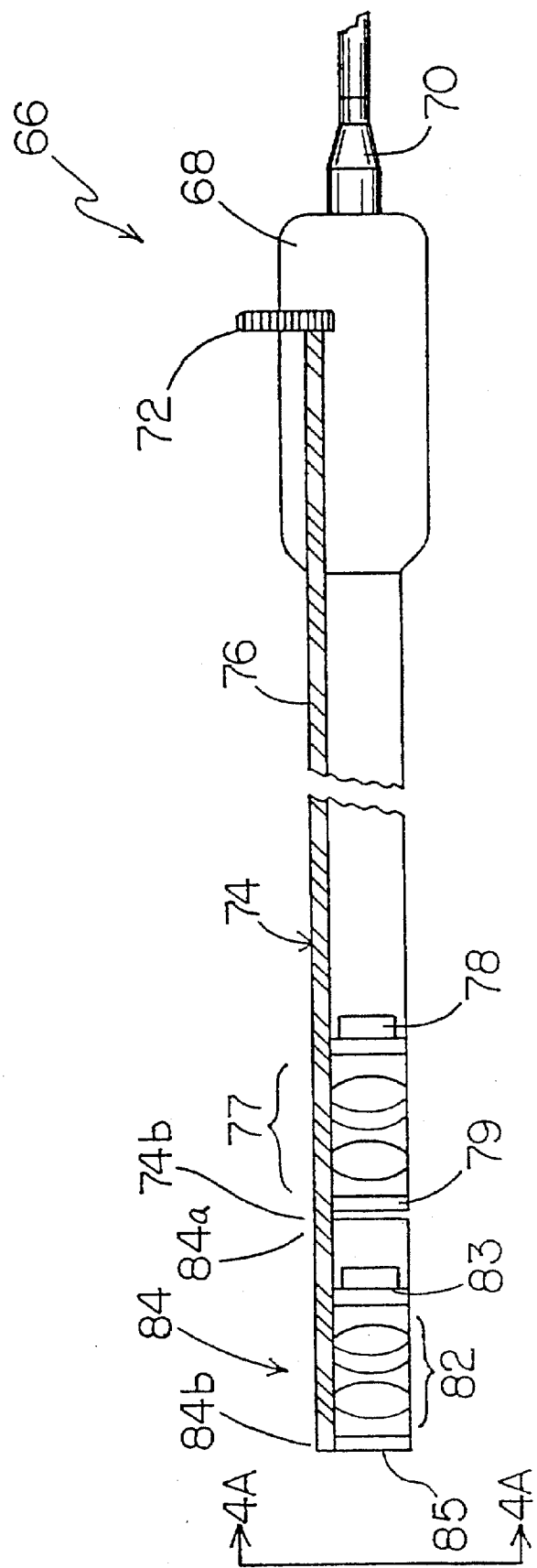
FIG. 4 is a top view of a stereoscopic endoscopic viewing system.

Referring now to FIGS. 1–1B, in which like elements are provided having like reference designations throughout the several views, an endoscope 10 includes a handle 16 having coupled to a back end 16a thereof an illumination fiber guide 12 and an electrical cable 14 which may be of the multiconductor type for example. A hollow tube 18 having a proximal end 18a and a distal end 18b is coupled to a front end 16b of the handle 16.

As can be more clearly seen in FIG. 1A, an aperture in the distal end 18B of the endoscope 10 has disposed therein a protective window 19 which preferably is manufactured from a material transparent to light. An optical train generally denoted 20 includes a first lens 20a disposed proximate the window 19, a second lens 20b and a third lens 20c disposed as shown.

A photodetector 22, which may be provided for example as a charge couple device (CCD) image sensor, is disposed at an end of the optical path 20 opposite the window 19. Such CCD image sensors are commercially available, and the operation of such devices is well known to those of ordinary skill in the art. For example a device manufactured by Panasonic Corporation and identified as part number MN3715FC may be used.

A plurality of electrical conductors 24a, 24b, 24c generally denoted 24 couple the photodetector 22 to the electrical cable 14. Second end of the electrical cable 14 may be coupled to a separate signal processing unit (not shown) as is generally known. A plurality of illumination fibers 28a–28N, generally denoted 28, are fed through the fiber guide 12 and terminate in the distal end 18b of the endoscope 10.

Referring briefly to FIG. 1B, the tube 18 is here provided as a pair of coaxial tubes 21a, 21b. An annular region 23 defined by an inner surface of the tube 21a and an outer surface of the tube 21b has disposed therein a plurality of illumination fibers 28.

Referring again to FIG. 1, a second end of the illumination fiber guide 12 is connected to a light source (not shown) which provides illuminating light to the optical fibers 28. A second end of the illumination fibers 28 are exposed through the annular aperture 23 to provide illumination to a region in front of the distal end 18b of the tube 18.

In use, the endoscope 10 may be inserted through a cannula and subsequently through an incision made in a body wall of a patient, for example, and disposed in a body cavity of the patient. Illuminating light fed from the light source (not shown) to the illumination fiber guide 12 travels along the fiber optic bundle 28 and illuminates a region in the patient's body cavity where the distal end 18b of the tube is disposed.

The optical train 20 receives light reflected from the body cavity through the window 19 and transmits an image from the distal end 18b of the tube 18 to the photodetector 22 via the optical train 20. The photodetector 22 converts the optical signals fed thereto to electrical signals which are fed on the electrical signal path 24 to the electrical cable 14. As mentioned above, the second end of the electrical cable 12 may be coupled to a signal processing unit and subsequently to a video monitor (not shown) as is generally known to allow the surgeon, for example, to view the area under operation. The window 19 may serve as an optical filter having filter characteristics selected to attenuate light which occurs at predetermined portions of the visual spectrum such that an image having desirable contrast and color may be viewed on the video monitor.

Conventional endoscopic viewing systems may typically include a plurality of lenses having relatively small diameters with each of the lenses arranged precisely in sequence to transmit an image from the distal end of the endoscope to a proximal or viewing end of the instrument where the image is focused onto the eye. In order to attach a video camera to the endoscope it is necessary to have an optical relay adapter to refocus the image onto the video camera. In conventional endoscopes, such small diameter lenses must be manufactured and assembled in a very precise manner.

In the present invention, however, the need for a complex optical train is eliminated because the photodetector 22 is disposed at the distal end of the endoscope 10. The replacement of the complex optical train with a relatively simple optical train 20 reduces the number of optical interfaces through which light must travel. This results in the endoscope of the present invention having a concomitant reduction in the attenuation of an image transmitted through the optical train 20. Thus, the light sensitivity of the endoscope 10 is significantly increased over conventional systems.

Furthermore, by providing the endoscope 10 having the shorter optical train 20 there is a significant reduction in the amount of chromatic aberration and geometrical distortions provided to an image. Moreover, the endoscope 10 may be provided in any length with no concomitant reduction in performance.

In conventional systems, the number of lenses which comprise the optical path is directly proportional to the length of the endoscope. The amount of light transmitted along the optical path is attenuated due to reflection and transmission losses resultant from each lens in the optical path. Thus, in conventional systems having a relatively long and complex optical train, light which is transmitted from the distal end to the proximal end of the endoscope may be highly attenuated.

In the present invention however, the image is converted to electrical signals in the distal end of the endoscope 10. Such electrical signals may be transmitted along an endoscope of any length with relatively little, if any, increase in signal loss. Thus, like optical trains having relatively low reflection and transmission loss characteristics may be used in endoscopes of any length with no corresponding reduction in image quality.

Furthermore, placing the photodetector 22 at the distal end 18b of the tube 18 reduces the amount of image eccentricity and eliminates the need for an optical relay coupling device which may provide image obscuration due to fogging during a surgical procedure. Such fogging generally occurs due to liquid sterilization and a wetness of the operational field due to irrigation of the operational field. Image eccentricity in conventional systems may be caused by the optical misalignment of the camera, the optical relay coupler, and the endoscope.

Referring now to FIGS. 2 and 2A an endoscope 30 includes a handle 32 having coupled to a back end 32a thereof an electrical cable 37 and having coupled to a front end 32b thereof a hollow tube 34 which may be similar to the tube 18 described above in conjunction with FIGS. 1–1B. Disposed in an aperture of a distal end 34b of the tube 34 is a window 36 and proximate the window 36 is disposed an optical train 38 and a photodetector 42. The window 36, optical train 38 and photodetector 40 may be similar to the window 19 (FIG. 1), the optical train 20 (FIG. 1) and the photodetector 22 (FIG. 1) described above in conjunction with FIGS. 1–1B. The photodetector 40 may be coupled to the electrical cable 37 via an electrical signal path 42 which includes electrical conductors 42a, 42b and 42c.

A light source 43 is disposed in a cavity region defined by the walls of the handle 32 of the endoscope 30. The handle 32 may be fabricated from a thermally conductive material such as aluminum for example to thus act as a heat sink to dissipate thermal energy by the light source 43. The electrical cable 37 includes a power cable 38 coupled to the light source 43. The light source 43 has coupled thereto fiber optic bundles 42a and 42b which are fed into the proximal end 34a of the tube 34. Although not shown in FIG. 2, a switch may be disposed on the handle and coupled between the power cable 38 and the light source 43 to thus provide a means for turning the light source 43 on and off.

As is clearly shown in FIG. 2B, the tube 34 is provided from a pair of coaxial tubes 35a, 35b. An inner surface of the tube 35a and an outer surface of the tube 35b defined an annular region 29. The fiber optic bundles 42a and 42b are dispersed and terminate in the distal end 34b of the tube 34 to provide a plurality of illumination fibers 44 evenly distributed in the annular region 29 between the pair of coaxial tubes 35a, 35b. The illumination of the viewing region is thus provided by light transmitted from the light source 43 to the fiber optic bundles 42a, 42b and consequently to the ends of the optical fibers 44.

As described above in conjunction with FIG. 1, by providing the photodetector 22 in the distal end of the endoscope 30 the transmission loss of the optical path is greatly reduced. Consequently, less light is required to provide adequate illumination in a desired region to be viewed such as a body cavity. Therefore, the optic light source 43 need not be as powerful as light sources used in conventional endoscopic viewing systems and may thus be disposed in the internal cavity region of the handle 32.

Referring now to FIGS. 3–3B, in which like elements are provided having like reference designations throughout the several views, an endoscope 50 includes a handle 52 having an electrical cable 53 coupled to a rear end thereof. It should be noted that the handle 52 here includes in an internal cavity region in which may be disposed an illumination assembly (not shown) similar to the illumination assembly 43 described above in conjunction with FIG. 2.

Alternatively, in the case where an illumination assembly is not disposed in a cavity region of the handle 52 an illumination guide (not shown) similar to the illumination guide 14 described above in conjunction with FIG. 1 may be coupled to the handle 52. Coupled to a front end of the handle 52 is a tube 54 having a proximal end 54a and a distal end 54b.

As may be more clearly seen in FIG. 3A, the tube 54 is provided from an inner tube 56 having a proximal end 56a (not shown) and a distal end 56b and an outer tube 57 having a proximal end 57a (not shown) and a distal end 57b. The proximal end of the inner tube is fixed to the handle 52 and an optics train rotating knob 55 (FIG. 3) is coupled to the proximal end of the outer tube 57. A photodetector 59 is disposed in the distal end 57b of the inner tube 56 and the photodetector 59 may thus be maintained in a predetermined orientation with respect to the handle 52 such that an image provided to the photodetector 59 may be transmitted via an electrical signal path provided by conductors 63a–63c, denoted generally as 63, in the same orientation to a viewing system (not shown).

A field widening lens 62 is disposed over an aperture in the distal end 57b of the outer tube 57. The field widening lens 62 may have the filtering characteristics similar to the window 19 described above in conjunction with FIG. 1. A prism 60 is disposed in the distal end 57b of the outer tube 57 to align an image fed thereto through the window field widening lens 62 with the lens system 58 which includes first and second lenses 58a and 58b as shown. Those of skill in the art will recognize of course that lens system 58 may include more or fewer lenses than those shown. The field widening lens 62, prism 60 and lens system 58 are fixed to the outer tube 57 and cooperate to provide an optical train. Thus, the outer tube 57 and consequently the optical train may be rotated via the optical train rotating knob 55. Since the photodetector 59 is disposed in a fixed position within the inner tube 56, an image seen on a viewing system (now shown) coupled to the photodetector 59 will not become disoriented with the rotating optical train.

The outer tube 57 may have the distal end 57b thereof terminated at an angle typically of about 15 to 45 degrees, however the termination angle may be in the range of 1 to 90 degrees. The angle of the prism face 60a is selected to correspond to the angle at which the distal end 57b of the tube 57 is terminated. Thus, the rotation of the tube 57 about its central longitudinal axis allows the surgeon to view a wider field of view. That is, the surgeon may view both forward and side regions of a viewing area by simply rotating the tube 57 and consequently the lens system 58, prism 60 and field widening lens 62 via the rotating knob 55.

For example, if the distal end of the tube 57 is terminated at an angle of 45° the endoscope 50 provides the surgeon having a view of a region at an angle of 45° from its central longitudinal axis and the surgeon is not limited to a straight view. Furthermore, in some applications it may be desirable for portions of either or both of the tubes 56, 57 proximate the proximal end of the tube 54 to be fabricated from a flexible material. It should be noted however that field widening lens 62, prism 60, lens system 58 and photodetector 59 should be aligned to provide proper optical focusing. When the outer tube 57 is rotated via the knob 55 the image which is transmitted through the angled end of the tube 57 is directed via the prism 60 and the lens system 58 to the photodetector 59 which may be provided as a CCD image sensor for example.

As described above in conjunction with FIG. 1, the photodetector 59 converts the optical signals to electrical signals and transmits them via electrical conductors 63a–63c, generally denoted 63, to the electrical cable 53 and subsequently to a video system or viewing system (not shown) coupled to the electrical cable 53. Thus the endoscope 50 simplifies the maneuvering and manipulation required of a surgeon, for example, to survey a 360° field of view while providing pictures having a constant orientation to a viewing system.

The prism 60 is here provided from three separate glass pieces joined to provide first and second reflecting surfaces 61a, 61b. Light enters the distal end of the tube 54 and enters the prism 60 through prism face 60a. The light ends the prism 60 and reflects off of the first reflective surface 61a, then reflects off the second reflective surface 61b and exits the prism 60 through prism face 60b. The light then passes into the lens system 58. As mentioned above, the lens system 58 is provided from two separate lenses 58a and 58b. Those of ordinary skill in the art will recognize of course that the lens system 58 may be provided from fewer or more lenses and the embodiment described herein is exemplary only.

In operation, the light reflected from the prism surface 61a is directed through the prism face 60b and toward the doublet formed by the convex-concave 58b and convex-convex lens 58a. The light is directed out of a second surface of the lens 58a and onto the photodetector 59 which converts the light image to electrical signals. The electrical signals are fed into an electrical signal processing system (not shown) and subsequently fed to a viewing system (not shown) via the electrical signal path 63 in a manner similar to that described above in conjunction with FIG. 1.

Figure 4A:
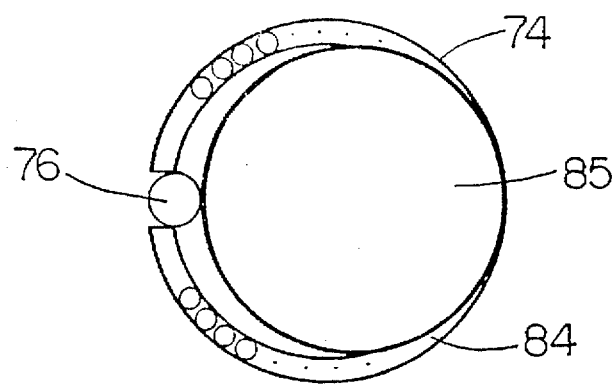
FIG. 4A is a front view of the stereoscopic endoscopic system of FIG. 4 of FIG. 1 but rotated 90 degrees counterclockwise from the FIG. 4 position.
Figure 4B:
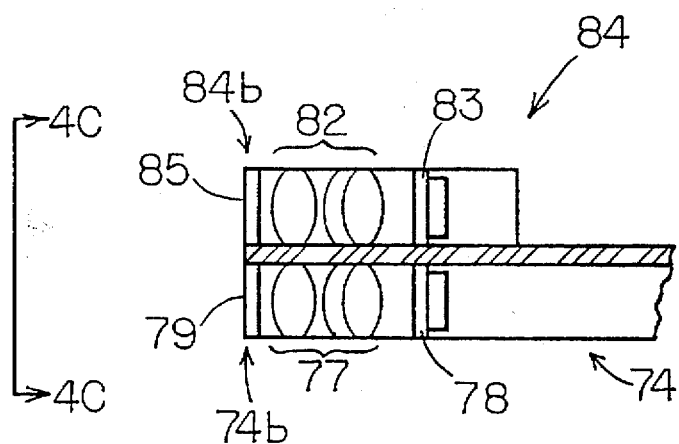
FIG. 4B is a top view of a portion of the stereoscopic endoscopic viewing system of FIG. 4A.
Figure 4C:
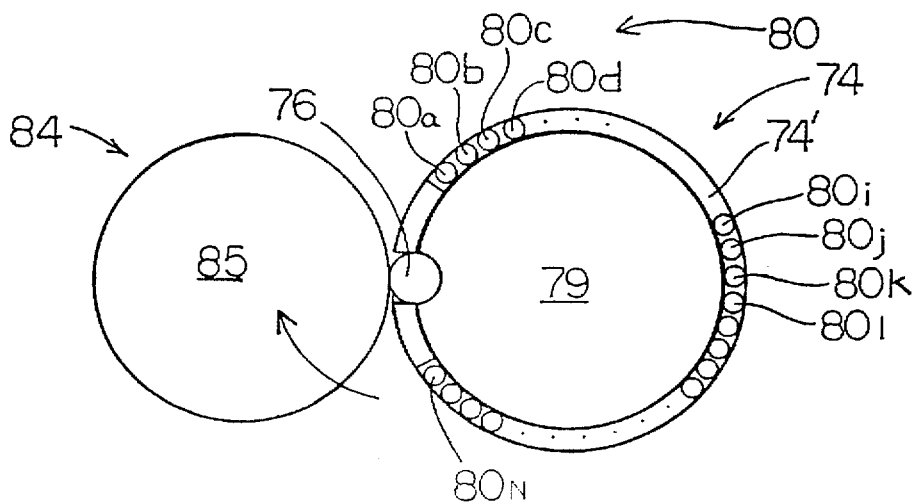
FIG. 4C is a front view of the stereoscopic endoscopic system of FIG. 4B but rotated 90 degrees counterclockwise from the FIG. 4 position.
Figure 4D:
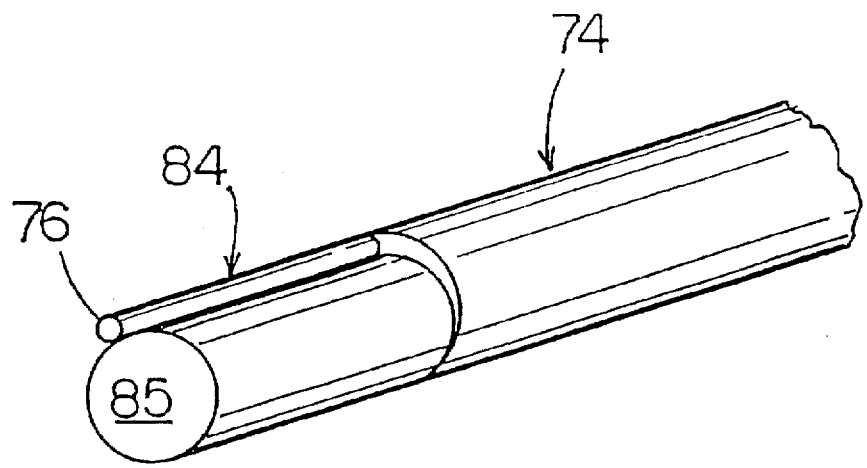
FIGS. 4D and 4E are perspective views of a portion of a stereoscopic viewing system which may be of the type shown in FIG. 4.
Figure 4E:
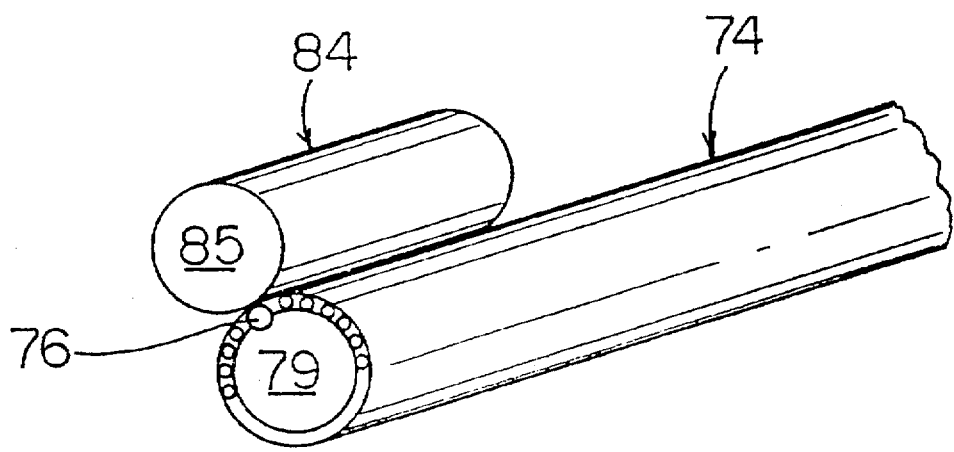

Referring now to FIGS. 4–4E, in which like elements are provided having like reference designations throughout the several views, a stereoscopic endoscopic viewing system 66 includes a handle 68 having an electrical cable 70 coupled to a rear surface thereof and having a lever 72 exposed through a top surface thereof. It should be noted that the handle 68 is here provided having an internal cavity region (not shown) in which is disposed an illumination assembly (not shown) similar to the illumination assembly 43 described above in conjunction with FIG. 2. Alternatively, in the case where an illumination assembly is not disposed in the handle 68 an illumination guide similar to the illumination guide 14 described above in conjunction with FIG. 1 may be coupled to the back surface of the handle 68.

A first hollow elongated tube 74 is coupled to a front surface of the handle 68. Tube 74 constitutes an outer tube 71 and a coaxial inner tube 73, as shown in FIG. 4C. A rod 76 here having a bore therethrough is disposed along a surface of the tube 74 and extends into the handle 68 and is coupled to the lever 72. A window 79 is disposed over an aperture in the distal end 74b of the tube 74. The window 79 may provide filtering characteristics similar to those of the window 19 described above in conjunction with FIG. 1. Disposed in the distal end of the tube 74 is a first optical train 77 and a photodetector 78 which may be provided as a CCD image sensor, for example.

A second tube 84 has a proximate end 84a juxtaposed the distal end 74b of the first tube 74. The second tube 84 has disposed therein a second optical train 82 and a second photodetector 83. A second window 85 is disposed over an aperture of a distal end 84b of the tube 84 as shown.

Referring briefly to FIGS. 4A and 4C, the illumination fibers 80a–80N generally denoted 80 are disposed in an annular region 74' between the tubes 71 and 73 that constitute the tube 74 in a manner similar to that described above in conjunction with FIG. 1B.

In FIG. 4, the second tube 84 is shown having a central longitudinal axis substantially aligned with a central longitudinal axis of the first tube 74. In operation, the tubes 74 and 84 are arranged such that the central longitudinal axis of each of the tubes 74, 84 fall on a single line as shown in FIG. 4 and may be inserted through a cannula through an incision made in a body wall of a patient for example. Once the tubes 74, 84 are passed through the cannula and are disposed in a body cavity of the patient, the lever 72 may be used to rotate the second tube 84 about the rod 76.

As may be more clearly seen in FIG. 4B, the second tube 84 may be rotated via the rod 76 until the central longitudinal axis of the tube 84 is adjacent and parallel with the central longitudinal axis of the first tube 74 and the window 79 of the first tube 74 is fully exposed. The lever 72 may be used to retract the distal end 84b of the second tube 84 until the distal end 84b of the second tube 84 and the distal end 74b of the first tube 74 are substantially aligned in a single plane as shown in FIG. 4D.

The image transmission elements may each be disposed at a slight angle toward each other such that the fields of view converge a single point. The angle may be present in the tubes 74, 84 to provide convergence at a predetermined nominal distance. Any resultant parallaxing for which results from viewing an object at a distance which is different than the nominal distance may be electronically compensated via a processor as is generally known to one of ordinary skill in the art Although not shown in FIG. 4 each of the photodetectors 78 and 83 are provided having electrical connections to the electrical cable 70. A plurality of electrical wires (not shown) from the second photo detector 83 are disposed through a bore in the rod 76 and coupled to the electrical cable 70.

The images are fed as electrical signals via the photodetectors 78, 83 to a stereo video processing unit (not shown). In the stereo processing unit (not shown) the electrical signals may be combined using computerized stereographic techniques.

Figure 5B:
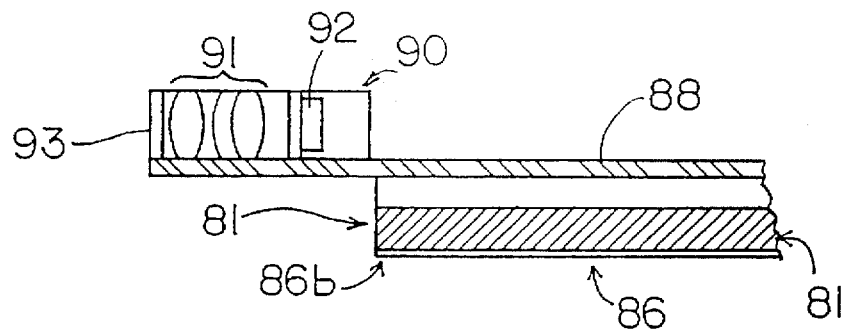
FIGS. 5–5D are a series of views of an endoscope having an operative channel.
Figure 5C:
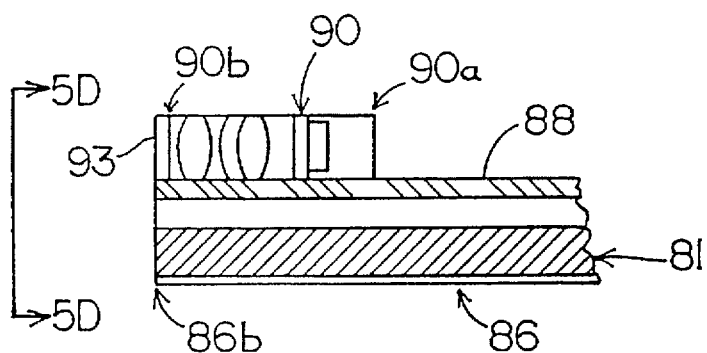
Figure 5D:
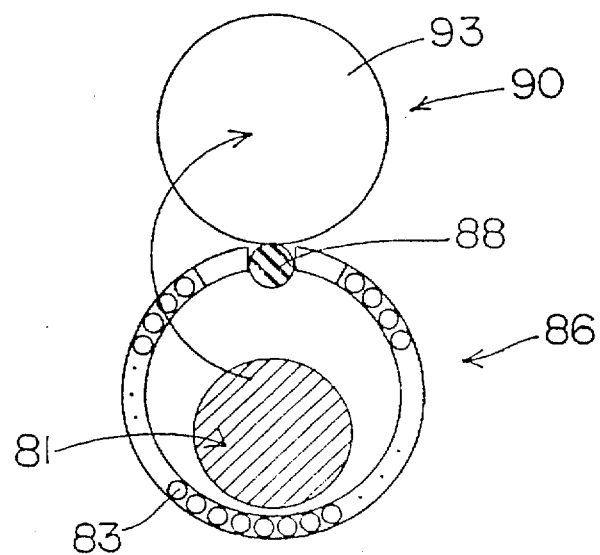

Referring now to FIGS. 5–5D, in which like elements are provided having like reference designations throughout the several views, an operative endoscope 80 includes a handle 82 having a pair of bores 81, 87 therethrough. An electrical cable 84 is coupled to a rear portion of the handle 82 in a manner and for a purpose the same as the electrical cables described hereinabove in conjunction with FIGS. 1, 2, 3 and 4. As mentioned above in conjunction with FIGS. 3 and 4, it should be noted that the handle 82 here includes in an internal cavity region (not shown) an illumination assembly (not shown) which may be similar to the illumination assembly 43 described above in conjunction with FIG. 2.

Alternatively, in the case where an illumination assembly is not disposed in the handle 82 an illumination guide similar to the illumination guide 14 described hereinabove in conjunction with FIG. 1 may be coupled to the handle 82.

A tube 86 is coupled to a front portion of the handle 82 and a rod 88 having a bore through at least a portion thereof is coupled to a top end of the tube and extends into the handle 82. The tube 86 is here shown being formed integrally as a unitary piece with the handle 82. It should be pointed out, however, that the handle 82 and the tube 86 may be formed as separate and distinct pieces and integrated using screws, epoxy or any other technique well known to those of ordinary skill in the art to join two pieces to provide one assembly. Tube 86 is a dual tube assembly like tubes 18, 34, 54 and 74, with a plurality of fiber optic rods 83 disposed in the annular space between its inner and outer tubes.

A knob 89 disposed in a top portion of the handle 82 is coupled to a first end of the rod 88. A second end of the rod 88 is coupled to a second hollow tube 90 having a proximate end 90a juxtaposed the distal end 86b of the first tube 86. A window 93 is disposed in an aperture of a distal end 90b of the second tube 90. The window 93 may provide the same filtering characteristics as the window 19 described in conjunction with FIG. 1 above. The second tube 90 is responsive to movements of the rod 88 and to movements of the knob 89. Disposed in the tube 90 is an optical train 91 and a photodetector 92.

A plurality of electrical wires from the photodetector 92 are disposed through the bore of the rod 88 and coupled to the electrical cable 84.

As may be more clearly seen in FIG. 5B, the second tube may be rotated 180° degrees via the rod 88 and positioned alongside the first tube 86. Thus, the bore 81 which passes through the handle 82 and the first tube 86 is exposed to provide an operative channel in which a surgical instrument (not shown) may be inserted. Also after the second tube 90 is rotated, the front ends of fiber optic rods 83 are exposed. The optic fibers 83 illuminate a region in front of the distal portion of the endoscope 80.

A stop cock 94 is coupled to the back end 85b of the handle 82. As is generally known an insufflation gas, such as carbon dioxide ($CO_2$) for example, is generally introduced into a patient to expand a body cavity and facilitate access to a surgical site. Here such gas may be introduced into the body cavity via the bore 87. Thus when no surgical instrument is disposed in the bore 81 the stop cock 94 may be closed to prevent the loss of the insufflation gas from the patients body cavity. The stop cock 94 may similarly operate to close the bore 87. Alternatively separate stop cocks (not shown) may be coupled to each of the bores 81, 87 to control the flow of gas through the bores 81, 87.

As may be more clearly seen in FIG. 5C the second tube 90 may be retracted such that the distal end 90b of the second tube 90 is substantially aligned in a single plane with the distal end 86b of the first tube 86. Thus any shadow effects caused by the tube 90 are minimized.

In operation, when the endoscope 80 is inserted through a cannula and into a body cavity of a patient to dispose tubes 86, 90 in the body cavity of the patient, a central longitudinal axis of the second tube 90 is aligned with a central longitudinal axis of the first tube 86. After the tubes 86 and 90 are disposed in the body cavity of the patient however, the second tube 90 may be rotated via the knob 89 and rod 88 to expose the operative bore 81 to thus allow a surgeon, for example, to pass a surgical instrument through the handle end of the bore 81 and perform surgery in the body cavity. After the surgery is complete, the surgical instrument is removed from the bore 81 and the second tube 90 may be rotated back into its original position having the central longitudinal axis substantially aligned with the central longitudinal axis of the first tube 86. The endoscope 80 may then be retracted from the body cavity and cannula Thus in the case where the endoscope 80 is inserted into the body cavity through a cannula (not shown), the inside diameter of the opening in the cannula determines the maximum outside diameter of the endoscope. Thus, in an endoscope having a predetermined outside diameter, the diameter of the operative channel in the present invention may be substantially larger than the diameter of the operative channel in conventional endoscopes.

That is for a predetermined outside diameter, the endoscope of the present invention is provided with an operative channel having a substantially larger diameter than the operative channel of a conventional operative endoscope having the same outside diameter. Thus, the operative channel 81 may be provided having a larger diameter than conventional endoscopes while the outside diameter of the tubes 86 and 90 remain the same as the outside diameter of a conventional endoscope. The surgeon, therefore, is provided with more room to insert a variety of different surgical instruments while preventing the need to provide a larger incision in the patient to accommodate an endoscope having a larger outside diameter. It will be also noted however that in some surgical procedures the operative endoscope may be used without the use of a cannula.

Figure 6:
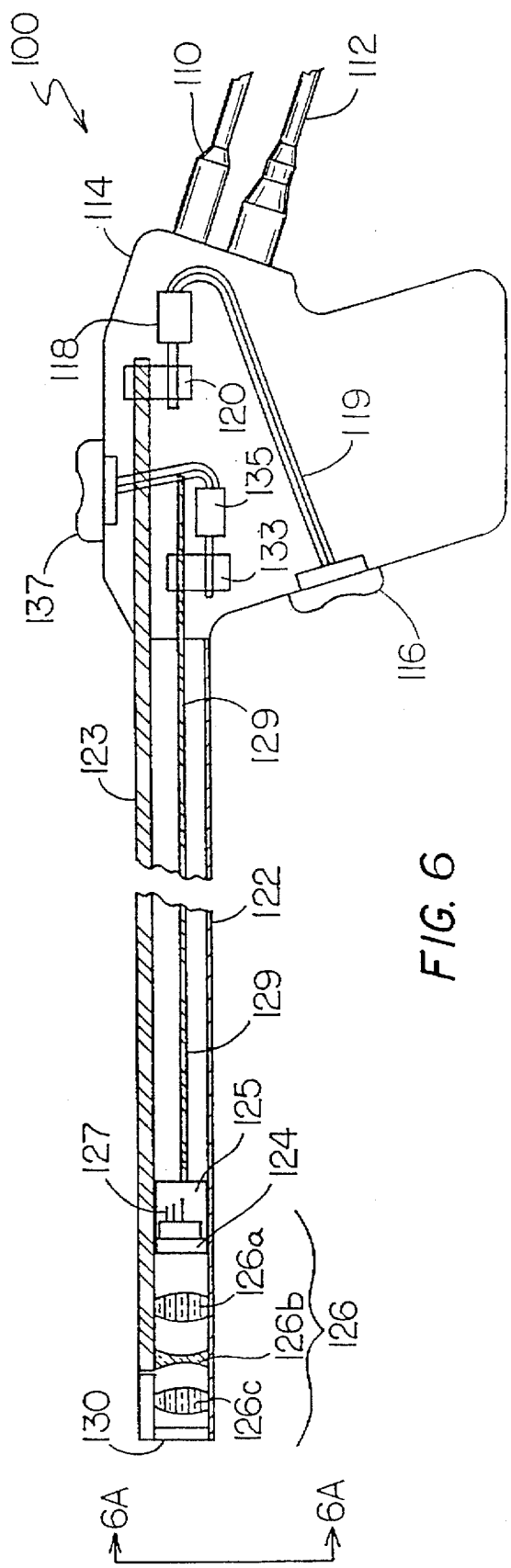
FIGS. 6–6B are a series of views of an endoscope having a zoom lens.
Figure 6B:
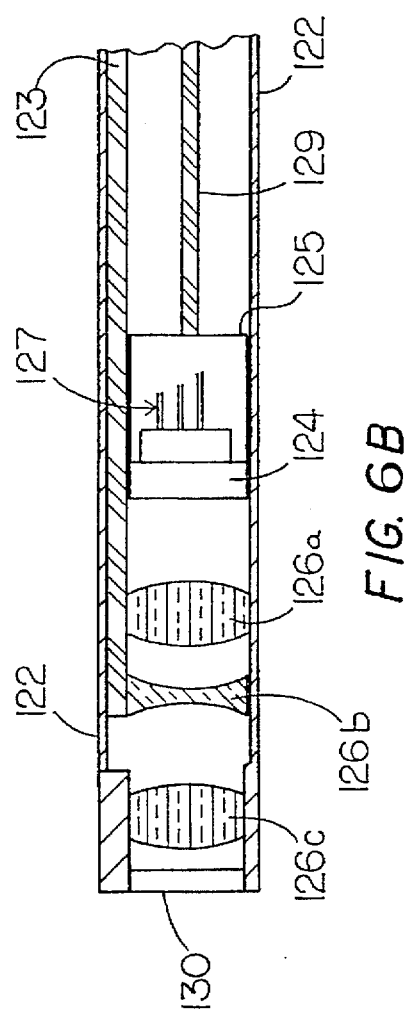
Figure 6A:
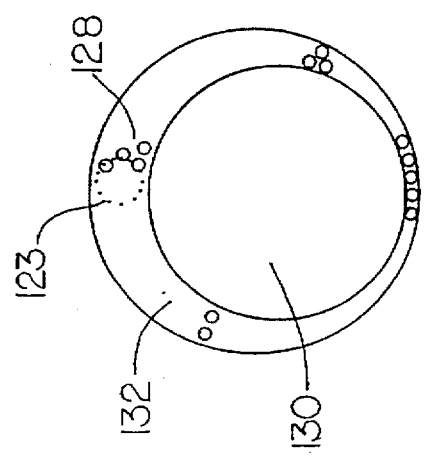

Referring now to FIGS. 6–6B, in which like elements are provided having like reference designations throughout the several views, an endoscope 100 includes a handle 114 having coupled to a back portion thereof an illumination fiber-guide 110. An electrical cable 112 is also coupled to the back portion of the handle 114.

It should be noted that the endoscope 100 here includes the illumination guide 110 coupled to the back portion of the handle 114 to perform the same function as the fiber guide 14 described above in conjunction with FIG. 1. In an alternate embodiment, the endoscope 100 may be provided having an illumination assembly (not shown) which may be similar to the illumination assembly 43 described hereinabove in conjunction with FIG. 2, for example, disposed in an internal cavity region of the handle 114.

A front portion of the handle 114 has coupled thereto a hollow tube 122 which, like tube 18, constitutes an inner tube and an outer tube, with optical rods or fibers disposed between the inner and outer tubes. In this case the inner and outer tubes are identified as 122a and 122b respectively and the optical rods or fibers are identified as 128. Coupled to the hollow tube is a rod 123. A bidrectional motor 118 is disposed in an internal cavity of the handle 114. The motor 118 may be coupled to the rod 123 via a motion-translating mechanism 120 which translates rotary motion of the output shaft of motor 118 into linear motion of rod 123. The motor is bi-directional so that it may move the rod 123 in two opposite directions.

A zoom control switch 116 is coupled between the electrical cable 112 and the motor 118. When the control switch 116 provides a first conductive path between a power line 119 and the motor 118, the motor 118 causes mechanism 120 to move control rod 123 in a first direction. When switch 116 provides a second conductive path between power line 119 and motor 118, the motor is reversed and hence causes the mechanism 120 to move control rod 123 in a second direction opposite to its first direction.

Disposed in the distal end of the hollow tube 122 is a photodetector 124 which may be provided as a CCD image sensor for example, and a plurality of lenses 126a, 126b and 126c. The lens 126b is slidably disposed in the tube 122. The rod 123 is coupled to the movable lens 126b while the lenses 126a, 126c are disposed in fixed predetermined positions within the tube 122. The lenses 126a, 126b and 126c together provide a lens train 126 which directs optical signals to photodetector 124. A lens 130, which may be similar to the lens 19 described above in conjunction with FIG. 1, may be disposed in the aperture of the inner tube 122a of tube 122.

The optical path 126 directs light to the photodetector 124 and as described above in conjunction with FIG. 1 the photodetector 124 converts the light to an electrical signal which may be fed to a viewing system (not shown) via the electrical signal path provided by conductors 127. In response to the motor 118 moving the rod 123, the lens 126b is moved relative to the lenses 126a and 126c in an axial direction Moving lens 126b changes the focal length of the lens train 126.

The photodetector 124 is disposed in a housing 125 that is movable within the inner tube 122a of hollow tube 122 in a direction along the longitudinal axis of the tube 122a. A second rod 129 is connected to the housing 125 and is also coupled to a second motion-translating mechanism 133 disposed inside the handle 114. A second bi-directional motor 135 is also disposed in an internal cavity of the handle 114. The second motor 135 is coupled to the second motion-translating mechanism. A focus control switch 137 is coupled between cable 112 and the second motor 135. When the switch 137 provides a first conductive path between a power source (not shown) and the motor 135, the second motor 135 causes the second motion-translating mechanism 133 to move the second control rod 129 in a axial first direction, thus moving the photodetector 124 in a first direction along the longitudinal axis of inner tube 122. When the switch 137 provides a second conductive path between the power source (not shown) and the motor 135, the motor 135 is reversed, whereby the second motion-translating mechanism 133 causes the second control rod 129 to turn in a second direction, thus moving the photodetector in a second opposite direction along the longitudinal axis of the tube 122. Therefore, the photodetector 124 may be moved relative to lens train 126 to obtain optimum focus.

As can be more clearly seen in FIG. 6B, the lens 126b may be moved relative to the lenses 126a, 126c and the photodetector 124. Depending on the distance by which a first surface of the lens 126b is separated from a first surface of the lens 126a a varying size image is provided to the photodetector 124. Thus, the surgeon may enlarge or reduce as desired the image of a particular feature of a body part to be operated on for example.

Figure 7:
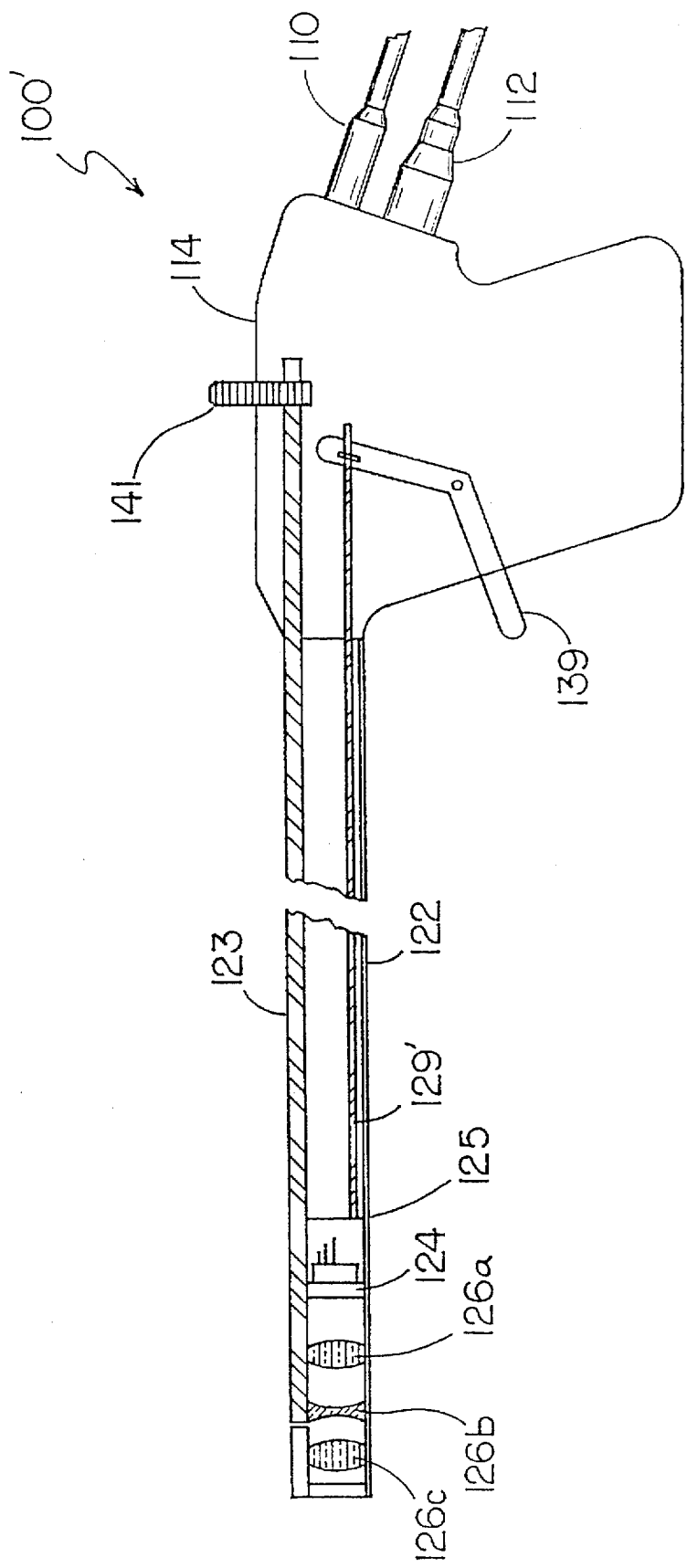
FIG. 7 is a view of an alternate embodiment of an endoscope having a zoom lens.

Referring now to FIG. 7, an alternate embodiment of the zoom endoscope 100' is shown to include a zoom control knob 141 coupled to the rod 123 to manually move the lens 126b. Similarly a focus control lever 139 is coupled to a rod 129' to manually move the photodetector 124 in first and second opposing directions along a longitudinal axis of the tube 122. Control lever 139 is pivotally attached to handle 114 as shown if FIG. 7. By moving the lens 126b relative to lens 126a, a particular magnification may be provided. However, such movement may defocus the viewing system. Thus, the focus control lever 139 may be used to move the photodetector 124 to an appropriate focal plane to thus provide a focused system.

Figure 7A:
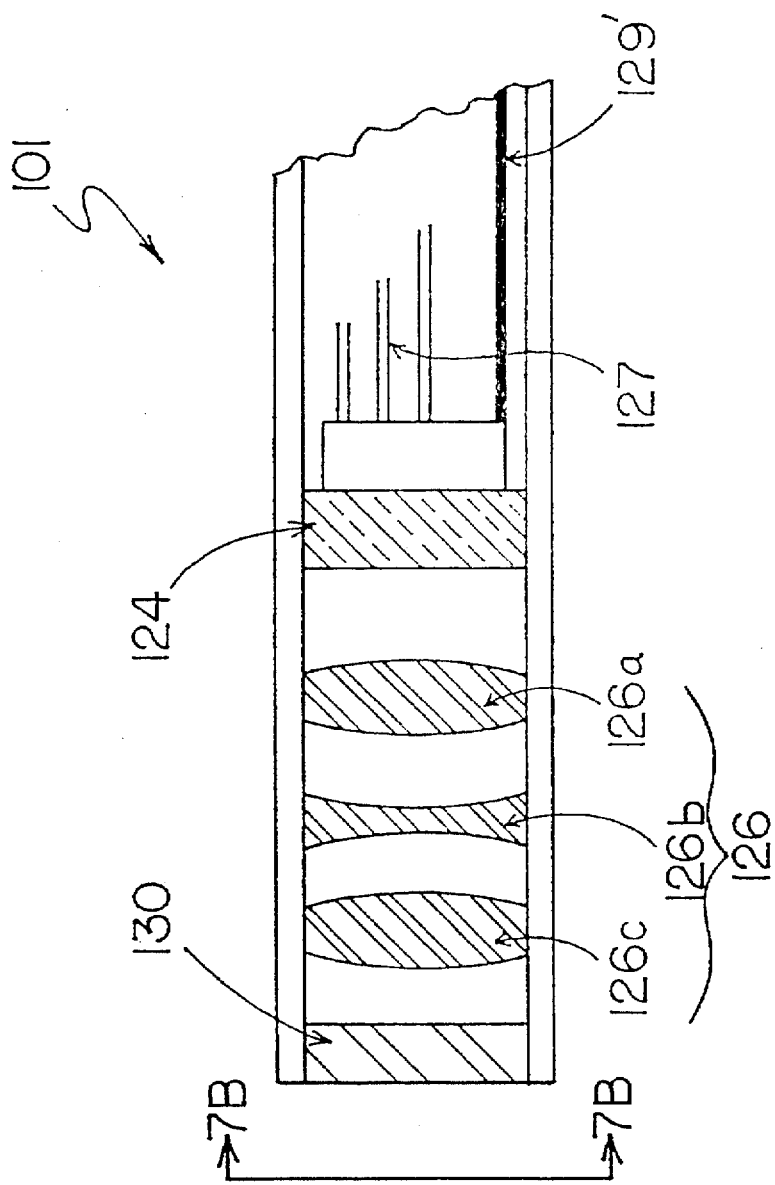
FIG. 7A is an alternate embodiment of an endoscope having a focusing mechanism which may be used in the endoscope of FIG. 7.
Figure 7B:
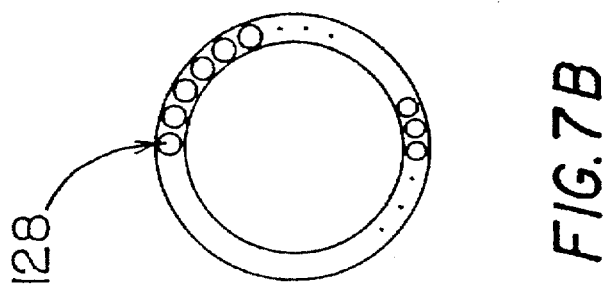
FIG. 7B is a front view of the endoscope of FIG. 7A.

Referring now to FIGS. 7A and 7B, a distal portion of an endoscope 101 includes a lens train 126 which directs optical signals to the photodetector 124 as described above in conjunction with FIGS. 6–6B. Endoscope 101 is a dual tube 18, with optical fiber 128 located between its inner and outer tubes. The photodetector 124 is directly coupled to a control rod 129'. The control rod 129' may be coupled at a second end thereof as described above in conjunction with FIG. 6. It should be noted that the optical path 126 is stationary while the image sensor 124 moves along first and second longitudinal directions in response to the control rod 129'. Thus, as shown in FIG. 7B, the optical fibers 128 may be evenly distributed about the circumference of the distal end of the endoscope 101.

Referring now to FIGS. 7C–7E, an endoscope 150 includes a rotatable optical train 152 which may be similar to the optical train described above in conjunction with FIGS. 3–3B and a moveable image sensor 154. The optical train 152 is disposed in a fixed position of the endoscope 150 and may be rotated in a manner as described in conjunction with FIGS. 3–3B above. The image sensor 154, however, is moveable along first and second longitudinal directions of the endoscope in response to movements of a control rod 155 moved by a lever 156. Thus, as shown in FIG. 7E, the optical fibers 128 may be evenly distributed about the circumference of the distal end of the endoscope 150.

Figure 8:
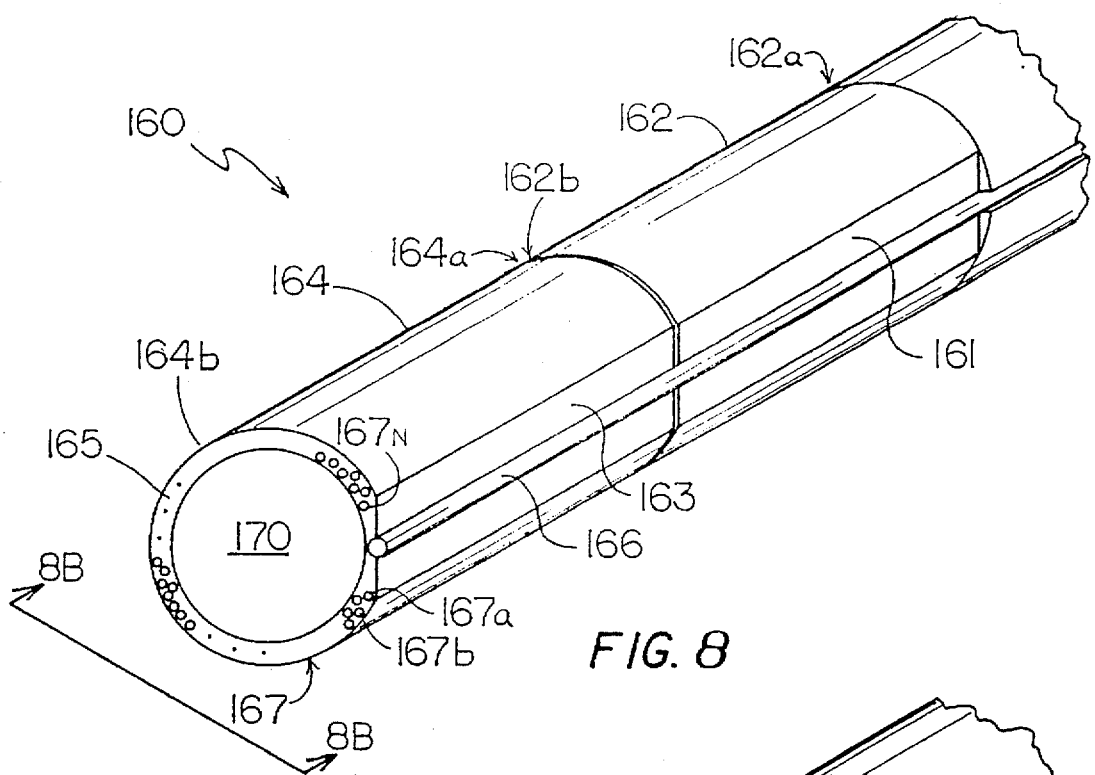
FIGS. 8–8E are a series of views of an endoscope having a parasitic set of fiber optic cables.
Figure 8A:
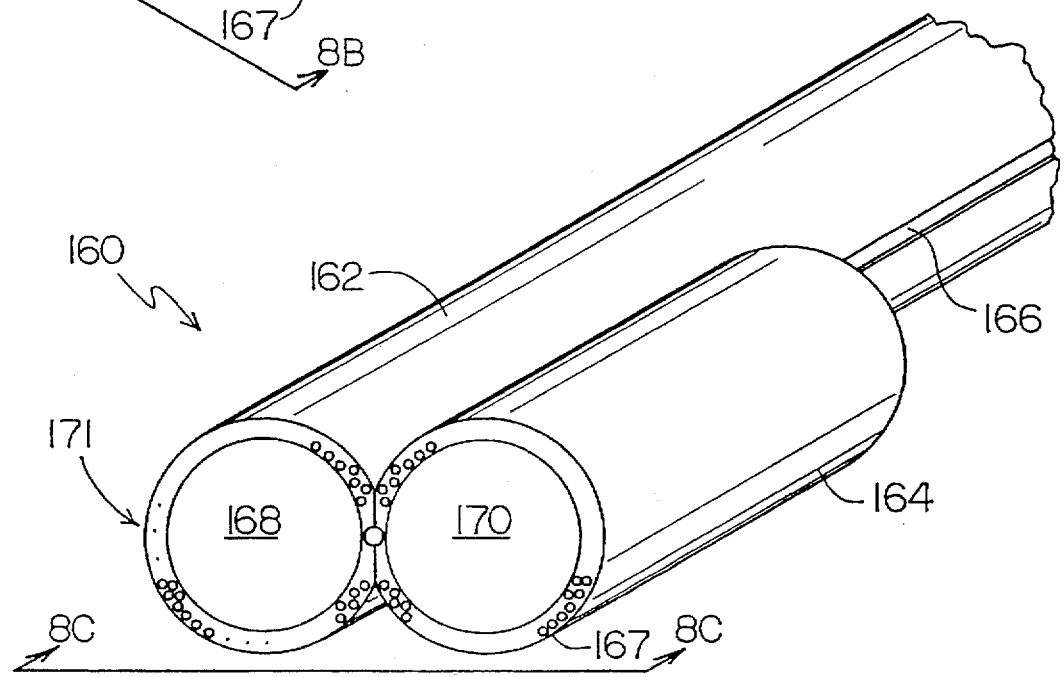
Figure 8B:
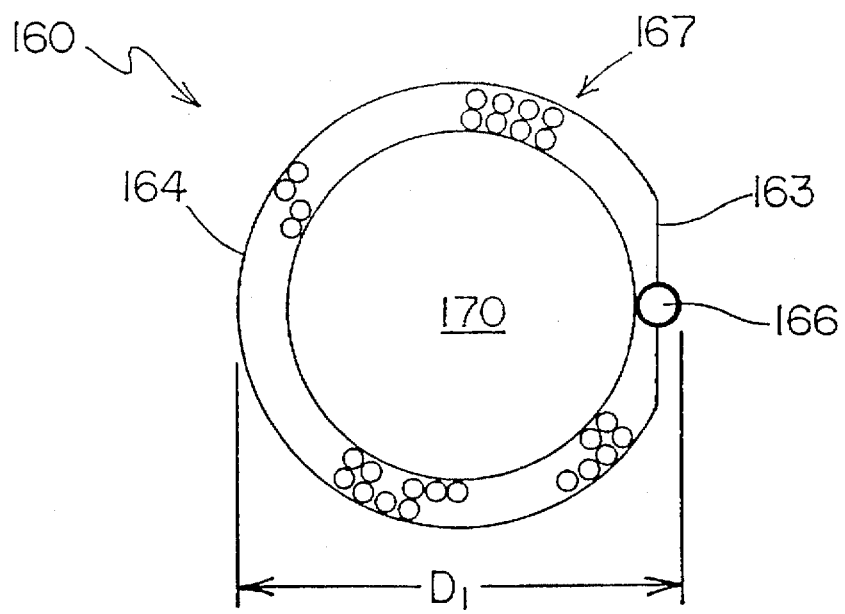
Figure 8C:
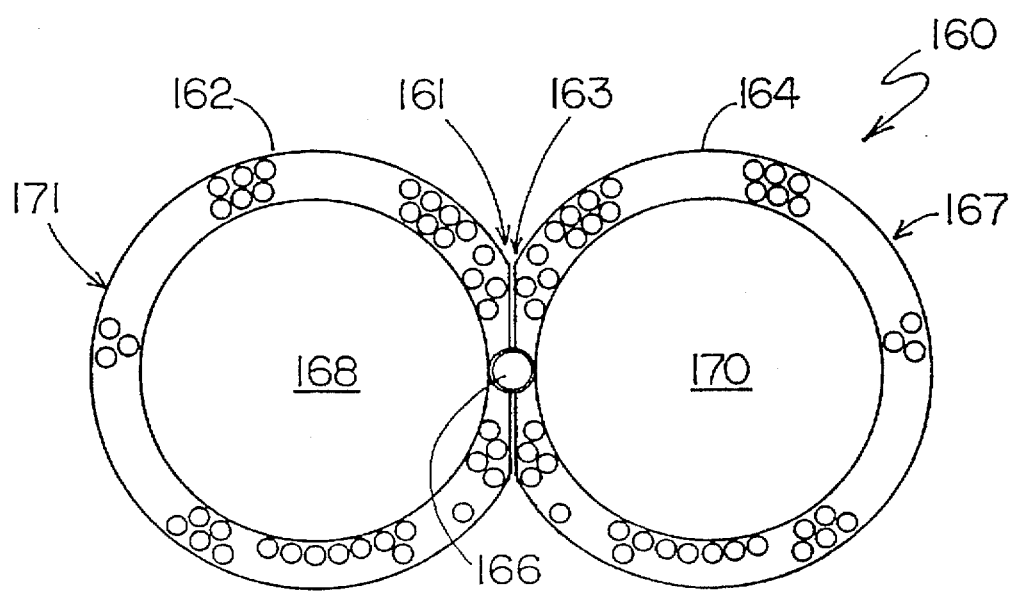

Referring now to FIGS. 8–8C, a distal portion 160 of an endoscope includes a first tube 162, a portion here being shown, and a second tube 164. The first and second tubes 162, 164 are each provided having flattened surfaces 161 and 163. A rod 166, which may be similar to the rod 76 described above in conjunction with FIG. 4, is disposed along the surfaces 161, 163 of the tubes 162 and 164 and is coupled to the tube 164. The outside diameter $D_1$ (FIG. 8B) of the endoscope 160 including the control rod 166 is selected to be smaller than an inside diameter of a cannula (not shown) through which the endoscope 160 may be disposed.

The second tube 164 has a proximate end 164a juxtaposed the distal end 162b of the first tube 162. Disposed in an annual aperture 165 of the second tube 164 are a plurality of illumination fibers 167a through 167N generally denoted 167. The illumination fibers 167 are disposed in the annular region 165 in a manner similar to that described in conjunction with FIGS. 1B, 4A and 4C.

In FIG. 8, the second tube 164 is shown having a central longitudinal axis substantially aligned with a central longitudinal axis of the first tube 162. In operation, the tubes 162 and 164 are arranged such that the central longitudinal axis of each of the tubes 162, 164 fall on a single line as shown in FIG. 8 such that the endoscope 160 may be inserted through a cannula (not shown) which has been inserted through an incision may in a body wall of a patient, for example. As may be clearly seen in FIG. 8B, the illumination fibers 167 are substantially aligned with the illumination fibers 171 when the first and second tubes 162 and 164 are aligned along a single longitudinal axis as shown in FIG. 8B.

As may be more clearly seen in FIG. 8A, the second tube 164 may be rotated via the rod 166 until the central longitudinal axis of the second tube 164 is adjacent and parallel with the central longitudinal axis of the first tube 162 to thus expose an aperture 168 of the first tube 162. After the tube 164 is rotated to expose the aperture 168, also exposed are a plurality of illumination fibers 171.

Thus, when the central longitudinal axes of the first and second tubes 162, 164 are aligned, a fiber optic light source (not shown) coupled to the illumination fibers 171 transmit light through the illumination fibers 167. The numerical aperture of the illumination fibers 171 are selected such that light is transmitted from the illumination fibers 171 and fed to the parasitic illumination fibers 167. Thus, the numerical aperture of the illumination fibers 167 is selected to be equal or greater than the numerical aperture of the illumination fibers 171.

When the first and second tubes 162, 164 are aligned, light is transmitted from the first illumination fibers 171 to the second set of illumination fibers 167. Thus, when the endoscope 160 is inserted through a cannula (not shown), at least a portion of and preferably all of the light is coupled from the illumination fibers 171 fed through the parasitic illumination fibers 167 to illuminate the region into which the endoscope 160 is being inserted.

The second tube 164 may be rotated via the rod 166 until a central longitudinal axis of the tube 164 is adjacent and parallel with the central longitudinal axis of the first tube 162 and the aperture 168 of the first tube 162 is fully exposed. The second tube 164 is rotated until the surface 164a is juxtaposed the surface 162a. The second tube 164 may then be retracted such that an aperture 170 of the second tube 164 is substantially in the same plane as the first tube aperture 168 (FIG. 8A).

When the second tube 164 is rotated to expose the aperture of the first tube, as shown in FIG. 8A, illumination fibers 171 provides illumination and 167 no longer have light fed thereto and thus do not provide illumination. Those of ordinary skill in the art will now recognize that this technique may be used, for example, in conjunction with the stereoscopic endoscopic described in conjunction with FIGS. 4 through 4E above or alternatively, the technique may be used in conjunction with the operative endoscope described in conjunction with FIGS. 5 through 5B above.

Figure 8D:
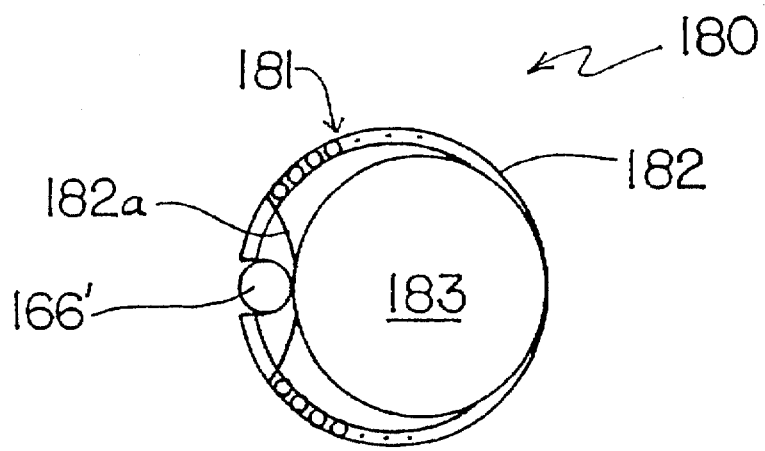
Figure 8E:
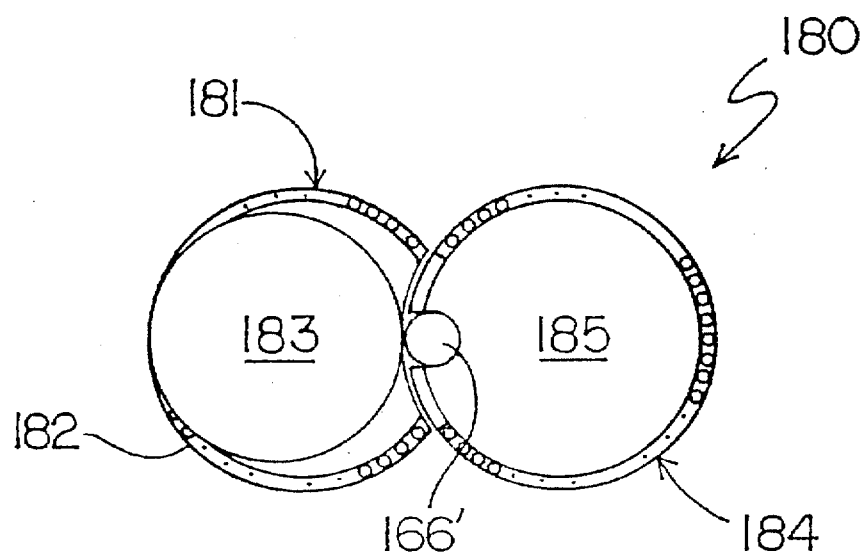

Referring now to FIGS. 8D and 8E, in an alternate embodiment, an endoscope 180 includes a tube 182 having parasitic illumination fibers 181 disposed thereon as shown. Here, the tube 182 is slightly offset about a central longitudinal axis of a first 184. Thus, as shown in FIG. 8E, only a portion of the illumination fibers 181 in the tube 182 may be aligned with the illumination fibers 186 disposed about the tube 184.

Here the outer surface of the tube 182 includes a contoured portion 182a. The contoured portion 182 is provided having a diameter corresponding to the outside diameter of the tube 184 such that when the tube 182 is rotated via a rod 166' to expose a front portion 185 of the tube 184, the tube 182 may be retracted along a side portion of the tube 184 without interference.

Figure 9:
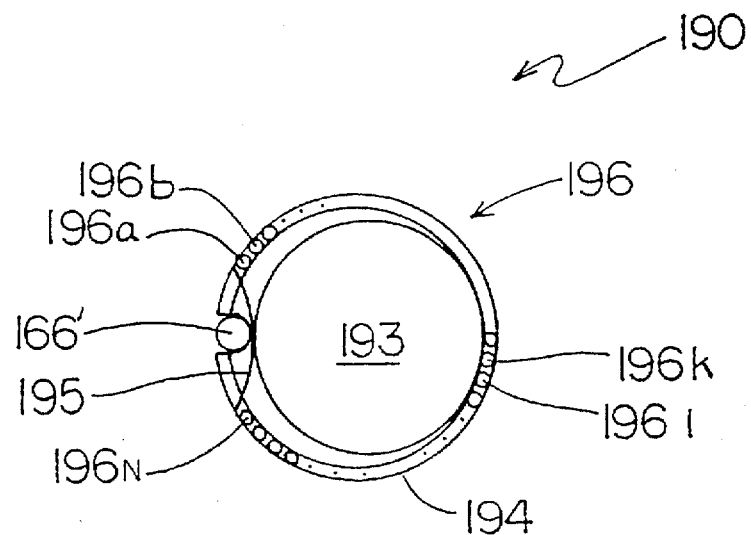
FIGS. 9 and 9A are front views of an alternate embodiment of an endoscope having parasitic illumination fibers.
Figure 9A:
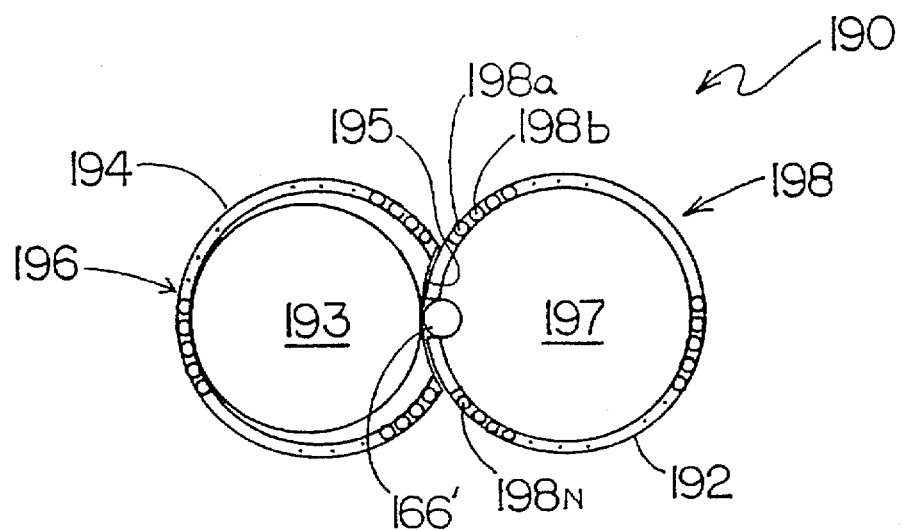

Referring now to FIGS. 9 and 9A, an endoscope 190 includes first and second tubes 192, 194. The second tube 194 is here provided having a diameter such that substantially all of the illumination fibers 196 in the second tube 194 may be disposed to receive light from illumination fibers 198 in the first tube 192. The illumination fibers 198 are coupled to a light source (not shown). Here the outer surface of the second tube 194 is includes a contoured portion 195. The contoured portion 195 is provided having a diameter corresponding to the outside diameter of the first tube 192 such that when the second tube 194 is rotated to expose a front portion 197 of the first tube 192, the second tube 194 may be retracted along a side portion of the first tube 192 without interference.

Having described preferred embodiments of the invention, it will now become apparent to one of skill in the art that other embodiments incorporating their concepts may be used. It is felt, therefore, that these embodiments should not be limited to disclosed embodiments but rather should be limited only by the spirit and scope of the appended claims.

What is claimed is:

1. An endoscope comprising:

a handle;

a tube assembly having a proximal end and a distal end, with said proximal end secured to said handle, said tube assembly comprising an inner tube an outer tube, and a plurality of fiber optic elements extending lengthwise of and disposed between said inner and outer tubes, each of said fiber optic elements having a first end and a second end with the first ends of said fiber optic elements terminating at the distal end of said tube assembly and the second ends of said fiber optic elements projecting out from the proximal ends of said tube assembly into a cavity in said handle;

a first bidirectional electric motor disposed in a cavity in said handle, said motor having a rotary output shaft;

a first lens disposed in said inner tube at the distal end of said inner tube;

a photodetector disposed in said inner tube at the distal end thereof proximate said first lens, said photodetector being movable lengthwise of said inner tube toward and away from said first lens;

a first control rod carried by said tube assembly, said first control rod having a first end and a second end with the first end of said first control rod being coupled to said photodetector; said control rod being movable lengthwise of said tube assembly, whereby to move said photodetector toward or away from said first lens;

a first gear mechanism disposed in a cavity in said handle, said first gear mechanism being coupled between the second end of said first control rod and said rotary output shaft of said first bidirectional motor for moving said first control rod lengthwise toward or away from said distal end of said tube assembly in response to operation of said first motor;

a second zoom lens disposed in said inner tube at said distal end thereof between said first lens and said photodetector; said zoom lens being movable lengthwise of said inner tube whereby to vary the magnification of the image that it transmits from said first lens to said photodetector;

a second bi-directional electric motor disposed in a cavity in said handle, said motor having a rotary output shaft;

a second control rod carried by said tube assembly, said second control rod having a first end and a second end with the first end of said second control rod being coupled to said zoom lens, said second control rod being movable lengthwise of said tube assembly, whereby to move said zoom lens toward or away from said first lens;

a second gear mechanism disposed in a cavity in said handle, said second gear mechanism being coupled between the second end of said second control rod and said rotary output shaft of said second bi-directional motor for moving said second control rod lengthwise toward or away from said distal end of said tube assembly in response to operation of said second motor;

means carried by said handle for injecting light into said second ends of said fiber optic elements;

first switch means carried by said handle and connected to said first motor for operating said first motor so as to selectively cause said first gear means to drive said first rod and thereby said photodetector in a first direction toward the distal end of said tube assembly or in a second direction away from said distal end of said tube assembly; and second switch means carried by said handle and connected to said second motor for operating said second motor so as to selectively cause said second gear means to drive said second rod and thereby said zoom lens in a first direction toward the distal end of said tube assembly or in a second direction away from said distal end of said tube assembly.

2. An endoscope according to claim 1 wherein said means for injecting light into said fiber optic elements comprises a light source disposed in a cavity region of said handle.

3. An endoscope according to claim 1 wherein said means for injecting light into said fiber optic elements comprises a flexible light-transmitting cable attached to and projecting from said handle for injecting light from a light source located outside of said handle.

4. An endoscope according to claim 1 wherein said photodetector is carried by a housing that is slidably disposed within said tube assembly, and further wherein said second rod is attached to said housing.

* * * * *

UNITED STATES PATENT AND TRADEMARK OFFICE
CERTIFICATE OF CORRECTION

PATENT NO. : 5,895,350
DATED : April 20, 1999
INVENTOR(S) : Koichiro Hori

It is certified that error appears in the above-indentified patent and that said Letters Patent is hereby corrected as shown below:

Claim 1, column 15, line 8, add a comma "," after the words -- inner tube --.

Signed and Sealed this

Twenty-seventh Day of July, 1999

Attest:

Q. TODD DICKINSON

*Attesting Officer*       Acting Commissioner of Patents and Trademarks